US012679923B2

(12) United States Patent
Zhu et al.

(10) Patent No.: US 12,679,923 B2
(45) Date of Patent: Jul. 14, 2026

(54) XYLYLENE DIISOCYNATE COMPOSITION, PREPARATION METHOD THEREFOR AND USE THEREOF

(71) Applicant: WANHUA CHEMICAL GROUP CO., LTD., Yantai (CN)

(72) Inventors: Fulin Zhu, Yantai (CN); Yonghua Shang, Yantai (CN); Jianfeng Li, Yantai (CN); Weijie Liu, Yantai (CN); Peng Wang, Yantai (CN); Wenbin Li, Yantai (CN); Pengfei Wang, Yantai (CN); Qian Wu, Yantai (CN); Wei Liu, Yantai (CN); Yuan Li, Yantai (CN)

(73) Assignee: WANHUA CHEMICAL GROUP CO., LTD., Yantai (CN)

( * ) Notice: Subject to any disclaimer, the term of this patent is extended or adjusted under 35 U.S.C. 154(b) by 426 days.

(21) Appl. No.: 18/281,208

(22) PCT Filed: Mar. 10, 2022

(86) PCT No.: PCT/CN2022/080069

§ 371 (c)(1),
(2) Date: Sep. 8, 2023

(87) PCT Pub. No.: WO2022/188825

PCT Pub. Date: Sep. 15, 2022

(65) Prior Publication Data

US 2024/0166795 A1 May 23, 2024

(30) Foreign Application Priority Data

Mar. 10, 2021 (CN) ......................... 202110262179.8
Mar. 7, 2022 (CN) ......................... 202210217405.5

(51) Int. Cl.

| | |
|---|---|
| ***C08G 18/71*** | (2006.01) |
| ***C07C 263/10*** | (2006.01) |
| ***C07C 263/20*** | (2006.01) |
| ***C07C 265/08*** | (2006.01) |
| ***C07C 265/14*** | (2006.01) |
| ***C08G 18/09*** | (2006.01) |
| ***C08G 18/10*** | (2006.01) |
| ***C08G 18/24*** | (2006.01) |
| ***C08G 18/32*** | (2006.01) |
| ***C08G 18/38*** | (2006.01) |
| ***C08G 18/42*** | (2006.01) |
| ***C08G 18/76*** | (2006.01) |
| ***C08G 18/79*** | (2006.01) |
| ***C08G 18/80*** | (2006.01) |
| ***C09D 175/04*** | (2006.01) |
| ***F21V 1/22*** | (2006.01) |
| ***G02B 1/04*** | (2006.01) |

(52) U.S. Cl.

CPC .......... *C08G 18/711* (2013.01); *C07C 263/10* (2013.01); *C07C 263/20* (2013.01); *C07C 265/08* (2013.01); *C07C 265/14* (2013.01); *C08G 18/092* (2013.01); *C08G 18/10* (2013.01); *C08G 18/242* (2013.01); *C08G 18/3206* (2013.01); *C08G 18/3876* (2013.01); *C08G 18/42* (2013.01); *C08G 18/7642* (2013.01); *C08G 18/794* (2013.01); *C08G 18/8029* (2013.01); *C09D 175/04* (2013.01); *G02B 1/04* (2013.01); *F21V 1/22* (2013.01); *G02B 1/041* (2013.01)

(58) Field of Classification Search

CPC .............. C08G 18/711; C08G 18/3876; C08G 18/7642; C08G 18/092; C08G 18/10; C08G 18/242; C08G 18/3206; C08G 18/42; C08G 18/794; C08G 18/8029; C07C 263/10; C07C 265/08; C07C 265/14; C07C 263/20; C09D 175/04; F21V 1/22; G02B 1/041; G02B 1/04

See application file for complete search history.

(56) References Cited

U.S. PATENT DOCUMENTS

| | | | | |
|---|---|---|---|---|
| 4,465,639 | A | 8/1984 | Hatfield | |
| 2016/0046565 | A1* | 2/2016 | Takamatsu | C07C 263/04 560/345 |
| 2019/0106529 | A1 | 4/2019 | Kuma | |
| 2019/0292304 | A1 | 9/2019 | Yamasaki et al. | |
| 2023/0340183 | A1* | 10/2023 | Kawaguchi | G02B 1/041 |

FOREIGN PATENT DOCUMENTS

| | | | |
|---|---|---|---|
| CN | 102070491 | A | 5/2011 |
| CN | 102516487 | A | 6/2012 |
| CN | 104945283 | A | 9/2015 |

(Continued)

OTHER PUBLICATIONS

Japanese Office Action , for JP Application No. 2023-555433, 6 pages, dated Jul. 19, 2024.
European Search Report, for EP Application No. 22766347.3, 7 pages dated Feb. 21, 2025.
Japanese Office Action, for JP Application No. 2023-555433, 6 pages, includes English Translation, dated Dec. 16, 2024.
Korean Notice, Third Party Observations for KR Application No. 10-2023-7031504, 4 pages, with English Translation, dated Jan. 15, 2024.
Japanese Notice to Grant for JP Application No. 2023555433, 5 pages, with English Translation, dated Jul. 7, 2025.

(Continued)

*Primary Examiner* — Rabon A Sergent
(74) *Attorney, Agent, or Firm* — Viksnins Harris Padys Malen LLP

(57) ABSTRACT

A xylylene diisocyanate composition, a preparation method therefor and the use thereof. The xylylene diisocyanate composition includes xylylene diisocyanate and 0.2-500 ppm of a compound represented by formula (1). A resin prepared from the provided xylylene diisocyanate composition has an excellent discoloration resistance and can effectively inhibit yellowing and/or white turbidity thereof.

15 Claims, 1 Drawing Sheet

(56) References Cited

FOREIGN PATENT DOCUMENTS

| | | | |
|---|---|---|---|
| CN | 105143178 | A | 12/2015 |
| CN | 106748887 | A | 5/2017 |
| CN | 107337615 | A | 11/2017 |
| CN | 108101810 | A | 6/2018 |
| CN | 108586705 | A | 9/2018 |
| CN | 109153637 | A | 1/2019 |
| CN | 110114339 | A | 8/2019 |
| CN | 111132960 | A | 5/2020 |
| CN | 111825572 | A | 10/2020 |
| CN | 113831262 | A | 12/2021 |
| CN | 114787230 | A | 7/2022 |
| EP | 4089071 | A1 | 11/2022 |
| GB | 834082 | A | 5/1960 |
| GB | 1194459 | A | 6/1970 |
| JP | H037253 | A | 1/1991 |
| JP | H10231344 | A | 9/1998 |
| JP | 2006273717 | A | 10/2006 |
| JP | 2014234429 | A | 12/2014 |
| JP | 6373536 | B1 | 7/2018 |
| JP | 2018193370 | A | 12/2018 |
| JP | 2019059823 | A | 4/2019 |
| JP | 2020024453 | A | 2/2020 |
| JP | 2021011959 | A | 2/2021 |
| JP | 2021091672 | A | 6/2021 |
| JP | 2024503332 | A | 1/2024 |
| KR | 20020010726 | A | 2/2002 |
| KR | 20150111360 | A | 10/2015 |
| WO | 2014163016 | A1 | 10/2014 |
| WO | 2015133485 | A1 | 9/2015 |
| WO | 2019235862 | A1 | 12/2019 |

OTHER PUBLICATIONS

International Search Report for PCT/CN2022/080069, 4 pages, dated Jun. 16, 2022. [English Translation].

Chinese Office Action , CN Application No. 202210217405.5, 6 pages, dated May 30, 2023.

Chinese Office Action , CN Application No. 202210217405.5, 3 pages, dated Jan. 18, 2023.

Zhang, G , et al., "Investigation on the Kinetics of XDI System Polymerization by IR Spectroscopy", Spectroscopy and Spectral Analysis, vol. 6, issue 5, 7 pages (1985).

* cited by examiner

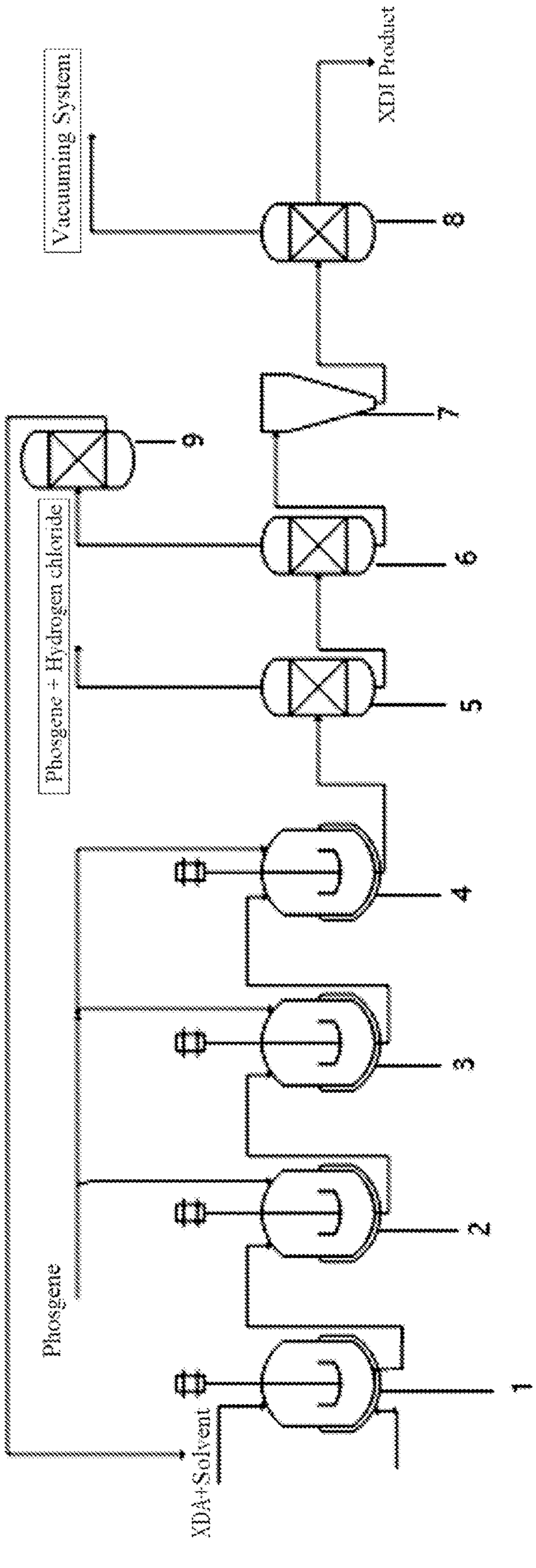
Vacuuming System
XDI Product
8
7
9
Phosgene + Hydrogen chloride
6
5
4
3
2
Phosgene
1
XDA+Solvent

XYLYLENE DIISOCYNATE COMPOSITION, PREPARATION METHOD THEREFOR AND USE THEREOF

CROSS-REFERENCE TO RELATED APPLICATION(S)

This patent application claims the benefit of priority of Chinese Patent Application Nos. 202110262179.8, filed on Mar. 10, 2021, and 202210217405.5, filed on Mar. 7, 2022.

TECHNICAL FIELD

The present application relates to the technical field of isocyanates, and in particular to a xylylene diisocyanate composition, a preparation method therefor and use thereof.

BACKGROUND

Xylylene diisocynate is an aliphatic isocyanate that has been used as a raw material for polyurethane resins in a variety of industrial products, and especially has a wide range of applications in optical materials. Xylylene diisocynate can be obtained by reacting xylylenediamine with phosgene (carbonyl chloride), which is known to produce chloride as a by-product when the reaction is carried out (see, for example, patent application GB1194459A).

However, for polyurethane resins, excellent color-changing resistance is required depending on the purpose and use. However, for polyurethane resins made from the xylylene diisocyanate documented in patent application GB1194459A, adequate color-changing resistance is sometimes not ensured.

Therefore, there is an urgent need in the field to provide a raw material of xylylene diisocyanate capable of stably manufacturing a resin with excellent color-changing resistance.

SUMMARY

The following is a summary of the subject matter described in detail herein. This summary is not intended to limit the scope of the claims.

In view of the shortcomings of the prior art, a first object of the present application is to provide a xylylene diisocyanate composition. A polyurethane resin prepared from the xylylene diisocyanate composition has excellent color-changing resistance.

To achieve this object, the present application adopts the following technical solutions.

The present application provides a xylylene diisocyanate composition, and the xylylene diisocyanate composition includes xylylene diisocyanate and 0.2-500 ppm (such as 0.4 ppm, 0.6 ppm, 0.8 ppm, 1 ppm, 5 ppm, 6 ppm, 10 ppm, 12 ppm, 15 ppm, 20 ppm, 40 ppm, 50 ppm, 60 ppm, 100 ppm, 150 ppm, 200 ppm, 210 ppm, 250 ppm, 300 ppm, 320 ppm, 350 ppm, 400 ppm, 450 ppm, 500 ppm, etc.) of a compound as shown in formula (1);

(1)

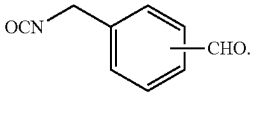

The researchers of the present application found that the resin prepared from the xylylene diisocyanate composition, which contains 0.2-500 ppm of the compound as shown in formula (1), has excellent color-changing resistance, and can be effectively inhibited in yellowing and/or white cloudiness. The content of less than 0.2 ppm or more than 500 ppm will lead to degraded color-changing resistance.

The xylylene diisocyanate composition of the present application is a substantially single compound (i.e., xylylene diisocyanate) containing more than 97 wt. % of xylylene diisocyanate as a main component, which, however, is defined as a xylylene diisocyanate composition because it contains the compound as shown in formula (1) as an accessory component.

In the present application, the xylylene diisocyanate composition is denoted as the XDI composition, the xylylene diisocyanate is denoted as XDI, and the compound as shown in formula (1) (isocyanatomethyl benzaldehyde) is denoted as IBA.

Preferably, the xylylene diisocyanate composition further includes a bromine-containing compound;

a content of the bromine-containing compound is 0.5-50 ppm based on a mass of elemental bromine, such as 1 ppm, 2 ppm, 3 ppm, 4 ppm, 5 ppm, 6 ppm, 7 ppm, 8 ppm, 9 ppm, 10 ppm, 11 ppm, 12 ppm, 13 ppm, 14 ppm, 15 ppm, 16 ppm, 17 ppm, 18 ppm 19 ppm, 20 ppm, 21 ppm, 22 ppm, 23 ppm, 24 ppm, 25 ppm, 26 ppm, 27 ppm, 28 ppm, 29 ppm, 30 ppm, 31 ppm, 32 ppm, 33 ppm, 34 ppm, 35 ppm, 36 ppm, 37 ppm, 38 ppm, 39 ppm, 40 ppm, 41 ppm, 42 ppm, 43 ppm, 44 ppm, 45 ppm, 46 ppm, 47 ppm, 48 ppm, 49 ppm, etc. If the bromine content is too high, the yellowing resistance of the prepared resin will be degraded, and if the bromine content is too low, the activity will be high and the prepared resin will be uneven.

In the present application, the contents of the compound as shown in formula (1) and the bromine-containing compound are both based on the total mass of the composition.

Preferably, the xylylene diisocyanate includes any one or a combination of at least two of 1,2-bis(isocyanatomethyl) benzene (o-xylylene diisocyanate, o-XDI), 1,3-bis(isocyanatomethyl) benzene (m-xylylene diisocyanate, m-XDI) or 1,4-bis(isocyanatomethyl)benzene (p-xylylene diisocyanate, p-XDI), preferably 1,3-bis(isocyanatomethyl)benzene and/or 1,4-bis(isocyanato methyl)benzene, and more preferably 1,3-bis(isocyanatomethyl)benzene.

Preferably, the compound as shown in formula (1) includes any one or a combination of at least two of the following compounds:

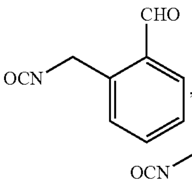
,
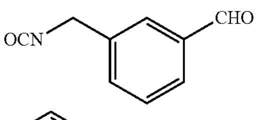
or
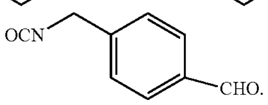

In the present application, IBA is produced as a by-product in the preparation of XDI as described later, of course, or is added artificially to obtain the required content. IBA includes o-IBA, m-IBA and p-IBA which are structural isomers. The XDI composition may contain one or more of these structural isomers of IBA.

In the present application, a containing proportion of IBA can be analyzed and determined by gas chromatography.

A second object of the present application is to provide a preparation method for the xylylene diisocyanate composition, and the preparation method includes:

(1) isocyanation process: subjecting xylylenediamine or xylylenediamine hydrochloride to isocyanation reaction with phosgene in the presence of a reaction solvent to obtain a reaction product containing xylylene diisocyanate and the compound as shown in formula (1);

(2) solvent separation and refining process: removing the solvent from the reaction product obtained in step (1), and refining the removed solvent to obtain a reuse solvent and then returning to the reaction system in step (1); and (3) separation process: separating and purifying the solvent-removed reaction product obtained in step (2) to obtain the xylylene diisocyanate composition.

The isocyanation process in step (1) can be called the phosgenation method, and the isocyanation reaction is the phosgenation reaction.

The phosgenation method specifically includes, for example, a method wherein xylylenediamine is reacted directly with phosgene (also known as a cold-hot two-stage phosgenation method), and a method wherein the hydrochloride obtained by reacting xylylenediamine with hydrochloric acid (hydrogen chloride) is reacted with phosgene in a reaction solvent (also known as an amine hydrochloride phosgenation method), and preferably the amine hydrochloride phosgenation method.

Preferably, the xylylenediamine hydrochloride is prepared via salt-forming process, and the salt-forming process includes: mixing xylylenediamine with hydrogen chloride in the presence of a reaction solvent and carrying out salt-forming reaction to obtain the xylylenediamine hydrochloride. The salt-forming process actually gives a slurry containing xylylenediamine hydrochloride, and the slurry is directly used in the isocyanation process.

Preferably, the xylylenediamine (XDA) includes any one or a combination of at least two of 1,2-bis(aminomethyl)benzene (o-xylylenediamine, o-XDA), 1,3-bis(aminomethyl)benzene (m-xylylenediamine, m-XDA) or 1,4-bis(aminomethyl)benzene (p-xylylenediamine, p-XDA).

Preferably, the salt-forming process specifically includes: introducing hydrogen chloride gas into the reaction solvent, then adding a reaction solvent amine solution containing xylylenediamine, and subsequently stirring and mixing the hydrogen chloride gas and the amine solution and carrying out salt-forming reaction to obtain the xylylenediamine hydrochloride.

Preferably, xylylenediamine in the amine solution has a content of more than or equal to 1.0 wt. %, such as 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, etc., and preferably more than or equal to 3.0 wt. %.

Preferably, xylylenediamine in the amine solution has a content of less than or equal to 50 wt. %, preferably less than or equal to 30 wt. %.

Preferably, a salt-forming temperature of the salt-forming process is more than or equal to 0° C., such as 1° C., 5° C., 10° C., 20° C., 30° C., 40° C., 50° C., 60° C., 70° C., 80° C., 90° C., 100° C., 110° C., 120° C., 130° C., 140° C., 150° C., etc., preferably more than or equal to 10° C.

Preferably, a salt-forming temperature of the salt-forming process is less than or equal to 160° C., preferably less than or equal to 150° C., and more preferably less than or equal to 140° C.

Preferably, the salt-forming process is carried out under atmospheric or pressurized conditions.

Preferably, a pressure (gauge pressure) of the salt-forming process is more than or equal to 0.01 MPaG, such as 0.1 MPaG, 0.2 MPaG, 0.5 MPaG, 0.6 MPaG, 0.7 MPaG, 0.8 MPaG, 0.9 MPaG, etc., and more preferably more than or equal to 0.02 MPaG.

Preferably, a pressure (gauge pressure) of the salt-forming process is less than or equal to 1.0 MPaG, preferably less than or equal to 0.5 MPaG, and more preferably less than or equal to 0.4 MPaG.

Preferably, step (1) specifically includes: introducing phosgene gas into xylylenediamine hydrochloride and carrying out isocyanation reaction to obtain a reaction product containing xylylene diisocyanate and the compound as shown in formula (1).

When xylylenediamine hydrochloride and phosgene are subjected to isocyanation reaction, the parameters below can be preferably selected to obtain the compound as shown in formula (1) with the target content. It should be noted that the containing proportion of IBA in the XDI composition can also be adjusted by adding IBA to the XDI composition.

Preferably, a molar amount of the phosgene is more than or equal to 4 times a molar amount of the xylylenediamine hydrochloride, such as 5 times, 6 times, 7 times, 8 times, 9 times, 10 times, 12 times, 14 times, 16 times, 18 times, 20 times, 22 times, 24 times, 26 times, 28 times, 30 times, 32 times, 34 times, 36 times, 38 times, 40 times, 42 times, 44 times, 46 times, 48 times, etc., preferably more than or equal to 5 times, and more preferably more than or equal to 6 times.

Preferably, a molar amount of the phosgene is less than or equal to 50 times a molar amount of the xylylenediamine hydrochloride, preferably less than or equal to 40 times, and more preferably less than or equal to 30 times.

Preferably, a reaction temperature of the isocyanation process is more than or equal to 80° C., such as 90° C., 100° C., 110° C., 120° C., 130° C., 140° C., 150° C., etc., and preferably more than or equal to 100° C.

Preferably, a reaction temperature of the isocyanation process is less than or equal to 180° C., preferably less than or equal to 170° C., and more preferably less than or equal to 160° C.

Preferably, a time of the isocyanation reaction is more than or equal to 2 h, such as 3 h, 4 h, 6 h, 8 h, 10 h, 12 h, 14 h, 16 h, 18 h, 20 h, 22 h, 24 h, etc., and preferably more than or equal to 4 h.

Preferably, a time of the isocyanation reaction is less than or equal to 25 h, and preferably less than or equal to 20 h.

Preferably, the isocyanation reaction is carried out under atmospheric or pressurized conditions.

Preferably, a pressure (gauge pressure) of the isocyanation reaction is more than or equal to 0 MPaG, such as 0.0004 MPaG, 0.0008 MPaG, 0.001 MPaG, 0.002 MPaG, 0.006 MPaG, 0.01 MPaG, 0.02 MPaG, 0.03 MPaG, 0.05 MPaG, 0.1 MPaG, 0.2 MPaG, 0.3 MPaG, 0.4 MPaG, 0.5 MPaG, 0.6 MPaG, etc., preferably more than or equal to 0.0005 MPaG, more preferably more than or equal to 0.001 MPaG, further preferably more than or equal to 0.003 MPaG, especially preferably more than or equal to 0.01 MPaG, particularly preferably more than or equal to 0.02 MPaG, and most preferably more than or equal to 0.03 MPaG.

Preferably, a pressure (gauge pressure) of the isocyanation reaction is less than or equal to 0.6 MPaG, preferably less than or equal to 0.4 MPaG, and more preferably less than or equal to 0.2 MPaG.

Preferably, the isocyanation process is intermittent process or continuous process, preferably continuous process.

The continuous process is the process where the slurry (XDA hydrochloride) produced in a stirring tank is continuously transported from the stirring tank to a reaction tank different from the stirring tank, the XDA hydrochloride is reacted with phosgene in the reaction tank, and a reaction solution (reaction substance) is continuously removed from the reaction tank. The number of reactors for the continuous process is not specifically limited in the present application, which, for example, may be two, three, four, five or more.

As needed, the reaction product of the isocyanation process can be subjected to gas removal process and solvent separation and refining process. The remaining carbonyl chloride phosgene, hydrogen chloride produced as a by-product and other gases are removed from the reaction product using a known gas removal column. In the solvent separation and refining process, the reaction solvent is distilled from the reaction solution using a known distillation column. After the solvent is refined, most of it is returned to the salt-forming and isocyanation process.

In the present application, the reaction solvent includes, for example, aromatic hydrocarbons such as benzene, toluene and xylene, aliphatic hydrocarbons such as octane and decane, alicyclic hydrocarbons such as hexamethylene, methylcyclohexane and ethylcyclohexane, halogenated aromatic hydrocarbons such as chlorotoluene, chlorobenzene, dichlorobenzene, dibromobenzene and trichlorobenzene, nitrogen-containing compounds such as nitrobenzene, N,N-dimethylformamide, N,N-dimethylacetamide and N,N'-dimethylimidazolinone, ethers such as dibutyl ether, ethylene glycol dimethyl ether and ethylene glycol diethyl ether, ketones such as heptanone, diisobutyl ketone, methyl isobutyl ketone and methyl ethyl ketone, aliphatic acid esters such as ethyl acetate, butyl acetate, pentyl acetate and ethoxyethyl acetate, aromatic carboxylic acid esters such as methyl salicylate, dimethyl phthalate, dibutyl phthalate and methyl benzoate, etc. The reaction solvent can be used alone or in a combination of two or more. The reaction solvent is preferably halogenated aromatic hydrocarbons, and more preferably chlorobenzene and dichlorobenzene.

The reaction solvent includes a fresh solvent and/or a reuse solvent; the "fresh solvent" refers to the reaction solvent which is subjected to the isocyanation process for the first time or the solvent added additionally with the solvent consumption in the system.

Preferably, a moisture content of the reaction solvent is 1-500 ppm, such as 2 ppm, 5 ppm, 10 ppm, 20 ppm, 30 ppm, 40 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 210 ppm, 220 ppm, 230 ppm, 240 ppm, 250 ppm, 260 ppm, 270 ppm, 280 ppm, 290 ppm, 300 ppm, 310 ppm, 320 ppm, 330 ppm 340 ppm, 350 ppm, 360 ppm, 370 ppm, 380 ppm, 390 ppm, 400 ppm, 410 ppm, 420 ppm, 430 ppm, 440 ppm, 450 ppm, 460 ppm, 470 ppm, 480 ppm, 490 ppm, etc.

Preferably, a moisture content of the reuse solvent is 1-500 ppm, such as 2 ppm, 5 ppm, 10 ppm, 20 ppm, 30 ppm, 40 ppm, 50 ppm, 60 ppm, 70 ppm, 80 ppm, 90 ppm, 100 ppm, 110 ppm, 120 ppm, 130 ppm, 140 ppm, 150 ppm, 160 ppm, 170 ppm, 180 ppm, 190 ppm, 200 ppm, 210 ppm, 220 ppm, 230 ppm, 240 ppm, 250 ppm, 260 ppm, 270 ppm, 280 ppm, 290 ppm, 300 ppm, 310 ppm, 320 ppm, 330 ppm 340 ppm, 350 ppm, 360 ppm, 370 ppm, 380 ppm, 390 ppm, 400 ppm, 410 ppm, 420 ppm, 430 ppm, 440 ppm, 450 ppm, 460 ppm, 470 ppm, 480 ppm, 490 ppm, etc.

In a preferred technical solution of the present application, the moisture content of the reuse solvent is controlled at 1-500 ppm, which is conducive to obtaining the composition with an IBA content of 0.2-500 ppm. If the moisture content is too high, the isocyanation process and separation process will have more side reactions, further leading to high IBA content. If the moisture content is too low, it will be difficult to produce IBA.

It should be noted that the fresh solvent with unqualified moisture content should firstly subjected to solvent refining after entering the system and, after obtaining qualified moisture content, then participates in the reaction.

The moisture content of the reaction solvent and/or the reuse solvent in the present application can be controlled by a solvent refining column.

Preferably, the solvent refining column includes a plate distillation column or a packed distillation column.

Preferably, a number of theoretical plates of the solvent refining column is more than or equal to 2, such as 4, 6, 8, 10, 14, 18, 22, 24, 26, 28, 30, 32, 34, 36, 38, 40, 42, 44, 46, 48, 50, 52, 54, 56, 58, etc., and preferably more than or equal to 5.

Preferably, a number of theoretical plates of the solvent refining column is less than or equal to 60, and preferably less than or equal to 40.

Preferably, an overhead pressure of the solvent refining column is more than or equal to 0.1 kPa, such as 0.2 kPa, 1 kPa, 5 kPa, 10 kPa, 30 kPa, 50 kPa, 70 kPa, 100 kPa, etc., and preferably more than or equal to 1 kPa.

Preferably, an overhead pressure of the solvent refining column is less than or equal to 300 kPa, and preferably less than or equal to 100 kPa.

Preferably, an overhead reflux ratio of the solvent refining column is more than or equal to 0.01, such as 0.05, 0.1, 0.5, 1, 2, 3, 4, 5, 6, 7, 8, 9, 10, 14, 18, 22, 24, 26, 28, 30, 32, 34, 36, 38, 40, 42, 44, 46, 48, 50, 52, 54, 56, 58, 60, 70, 80, 90, etc., and preferably more than or equal to 5.

Preferably, an overhead reflux ratio of the solvent refining column is less than or equal to 100, and preferably less than or equal to 90.

Preferably, a moisture content of the reuse solvent is 1-500 ppm, such as 10 ppm, 20 ppm, 40 ppm, 50 ppm, 80 ppm, 100 ppm, 120 ppm, 140 ppm, 160 ppm, 180 ppm, 200 ppm, 220 ppm, 240 ppm, 260 ppm, 280 ppm, 300 ppm, 320 ppm, 340 ppm, 360 ppm, 380 ppm, 400 ppm, 420 ppm, 440 ppm, 460 ppm, 480 ppm, etc.

As needed, the reaction product with solvent removed can be subjected to tar removal process. The tar component is removed from the reaction solution using a known tar removal device such as a short-range evaporator. It should be noted that a reaction substance that has been removed the tar component by the tar removal process is denoted as an intermediate substance.

In addition, as needed, the intermediate substance can be distilled and purified. The purification method is not particularly limited and can be carried out via industrial separation techniques, such as distillation, crystallization precipitation, etc.

Preferably, the distillation is carried out in a distillation column.

Preferably, the distillation column includes a plate distillation column or a packed distillation column.

In a preferred technical solution of the present application, the IBA proportion can be adjusted to the above-mentioned range by controlling the reaction conditions and separation conditions.

It should be noted that the containing proportion of IBA in the XDI composition can also be adjusted by adding IBA to the XDI composition.

Preferably, a number of theoretical plates of the distillation column is more than or equal to 2, such as 4, 6, 8, 10, 14, 18, 22, 24, 26, 28, 30, 32, 34, 36, 38, 40, 42, 44, 46, 48, 50, 52, 54, 56, 58, etc., and preferably more than or equal to 5.

Preferably, a number of theoretical plates of the distillation column is less than or equal to 60, and preferably less than or equal to 40.

Preferably, an overhead pressure of the distillation column is more than or equal to 0.1 kPa, such as 0.2 kPa, 0.4 kPa, 0.6 kPa, 0.8 kPa, 1 kPa, 1.5 kPa, 2 kPa, 2.5 kPa, 3 kPa, 3.5 kPa, etc., and preferably more than or equal to 0.15 kPa.

Preferably, an overhead pressure of the distillation column is less than or equal to 4 kPa, and preferably less than or equal to 2.5 kPa.

Preferably, an overhead reflux ratio of the distillation column is more than or equal to 0.01, such as 0.05, 0.1, 0.5, 1, 2, 3, 4, 5, 6, 7, 8, 9, 10, 14, 18, 22, 24, 26, 28, 30, 32, 34, 36, 38, 40, 42, 44, 46, 48, 50, 52, 54, 56, 58, etc., and preferably more than or equal to 0.1.

Preferably, an overhead reflux ratio of the distillation column is less than or equal to 60, and preferably less than or equal to 40.

In a preferred technical solution of the present application, the preparation method for the XDI composition can be carried out, for example, via the device flow chart shown in FIG. 1. As shown in FIG. 1, a salt-forming reactor 1 is mainly included, in the isocyanation unit as described later, 3-stage continuous isocyanation process is carried out (via a first phosgenation reactor 2, a second phosgenation reactor 3 and a third phosgenation reactor 4 in sequence), and the production amounts of XDI and IBA are adjusted by appropriately adjusting the moisture content of the solvent, the feeding proportion of phosgene, the reaction temperature, the reaction pressure and the average residence time, etc. After the phosgenation reactors, a phosgene removal column 5 and a solvent removal column 6 are arranged to remove phosgene and solvent from the reaction solution, and the solvent is subjected to a solvent refining column 9 to control the moisture content and then reused. And after the solvent removal column 6, a tar removal device 7 is arranged to subject the reaction product with solvent removed to tar removal process, and then the reaction product is subjected to a rectification column 8 for rectification to obtain the final product.

Moreover, the containing proportion of IBA in the XDI composition is adjusted by appropriately adjusting the overhead reflux ratio and the like in the rectification separation as described later.

Specifically, firstly, the reaction solvent is loaded into the salt-forming reactor. Then, hydrogen chloride gas is continuously fed to the bottom of the salt-forming reactor through a hydrogen chloride feeding pipeline according to the feeding proportion. In addition, the amine solution with XDA dissolved in the reaction solvent is continuously fed to the top of the salt-forming reactor through an amine feeding pipeline. Then, while maintaining the salt-forming temperature and pressure inside the salt-forming reactor, the hydrogen chloride gas and the amine solution are stirred and mixed by stirring blades (salt-forming process). Accordingly, a slurry containing XDA hydrochloride is prepared.

Then, the slurry containing XDA hydrochloride is continuously delivered to the top of the phosgenation reactor through a hydrochloride delivery pipeline. In other words, the slurry containing XDA hydrochloride is continuously removed from the salt-forming reactor and delivered to the phosgenation reactor while the hydrogen chloride gas and amine solution are continuously fed to the salt-forming reactor.

Subsequently, the phosgene is continuously fed to the respective top of the first phosgenation reactor, the second phosgenation reactor and the third phosgenation reactor via inserting tubes according to the feeding proportion. Then, the slurry and phosgene are stirred and mixed while the first phosgenation reactor is maintained at the reaction temperature and reaction pressure inside (the first stage of the isocyanation process). As a result, XDA hydrochloride reacts with carbonyl chloride to produce XDI as the main component as well as IBA and the bromine-containing compound or its intermediates as by-products.

Then, the reaction solution containing XDI, IBA and the bromine-containing compound and the reaction solvent is continuously delivered to the top of the second phosgenation reactor through a reaction substance delivery pipeline. In other words, the slurry and phosgene are continuously fed to the first phosgenation reactor while a first phosgenation solution is continuously removed from the first phosgenation reactor and delivered to the second phosgenation reactor.

Subsequently, the first reaction substance and phosgene are stirred and mixed in the second phosgenation reactor while the second phosgenation reactor is maintained at the reaction temperature and reaction pressure inside (the second stage of isocyanation process).

Similarly, the third phosgenation reactor is also used for the phosgenation reaction while a secondary reaction substance is input (the third stage of isocyanation process).

Thus, the salt-forming process and the isocyanation process are carried out continuously.

After that, the reaction solution is prepared which contains XDI, IBA and the bromine-containing compound or its intermediates and the reaction solvent. It should be noted that the sum of the residence time of the three isocyanation process stages falls within the range described above.

Subsequently, the phosgenation reaction solution is continuously delivered to the middle of the phosgene removal column through the reaction substance delivery pipeline. The phosgenation solution is separated into a gas containing phosgene and hydrogen chloride, etc., and a liquid gas-removed substance containing XDI, IBA and the bromine-containing compound or its intermediates and the reaction solvent via the phosgene removal column (gas removal process).

Subsequently, the gas-removed substance is continuously delivered to the middle of the solvent removal column through a gas-removed substance delivery pipeline. Then, the reaction solvent is distilled from the gas-removed substance via the solvent removal column (solvent separation and refining process) to obtain a solvent-removed substance containing XDI, IBA and the bromine-containing compound or its intermediates.

The reaction solvent is returned to the salt-forming and phosgenation reaction system via the solvent refining column, and the moisture content of the reuse solvent is controlled by controlling the operating conditions of the column (overhead pressure, overhead reflux ratio, and residence time).

Subsequently, the solvent-removed substance is continuously delivered to the top of the tar removal device through a solvent-removed substance delivery pipeline. Then, the tar component is removed from the solvent-removed substance by the tar removal device to obtain an intermediate substance containing XDI, IBA and the bromine-containing compound (tar removal process).

Subsequently, the intermediate substance is continuously delivered to the middle of the rectification column through an intermediate substance delivery pipeline. Then, under the conditions of the rectification process described above (bottom temperature, overhead temperature, overhead pressure, bottom reflux ratio, overhead reflux ratio and residence time), the low-boiling material is distilled away from the intermediate and the XDI composition is collected from the lower middle of the column.

As a result, the XDI composition can be continuously prepared which contains XDI, IBA and the bromine-containing compound.

A third object of the present application is to provide a modified composition of a xylylene diisocyanate composition, wherein the modified composition is obtained by modifying the xylylene diisocyanate composition according to the first object, and the modified xylylene diisocyanate in the modified composition includes any one or a combination of at least two of groups (a)-(e) as follows: (a) an isocyanurate group, (b) a uretdione group, (c) a biuret group, (d) a carbamate group, (e) a ureido group, (f) an iminooxadiazinedione group, (g) an allophanate group, (h) a uretonimine group or (i) a carbodiimide group.

Those skilled in the art can modify the XDI composition using known methods as needed to obtain the modified XDI composition, which, as a polyisocyanate component, can be suitably applied to a raw material of polyurethane resins together with a component having an active hydrogen group.

More specifically, the modified XDI having the functional group (a) (isocyanurate group) is a trimer of XDI, which can be obtained, for example, by reacting the XDI composition in the presence of a known isocyanurate-forming catalyst to subject XDI therein to isocyanurate formation.

The modified XDI having the functional group (b) (allophanate group) can be obtained by subjecting the XDI composition to further reaction in the presence of a known allophanate-forming catalyst after reacting with alcohol.

The modified XDI having the functional group (c) (biuret group) can be obtained by subjecting the XDI composition to further reaction in the presence of a known biuret-forming catalyst after reacting with, for example, water, tertiary alcohol (such as tert-butanol), secondary amine (such as dimethylamine and diethylamine), etc.

The modified XDI having the functional group (d) (carbamate group) can be obtained by reacting the XDI composition with a polyol component (such as trimethylolpropane).

The modified XDI having the functional group (e) (ureido group) can be obtained by reacting the XDI composition with water, a polyamine component (as described later), etc.

The modified XDI (asymmetric trimer) having the functional group (f) (iminooxadiazinedione group) can be obtained by reacting the XDI composition in the presence of a known iminooxadiazinedione-forming catalyst to subject XDI therein to iminooxadiazinedione formation (such as trimerization).

The modified XDI having the functional group (g) (uretdione group) can be obtained by heating the XDI composition at about 90° C.-200° C. or by reacting the XDI composition in the presence of a known uretdione-forming catalyst to subject XDI therein to uretdione formation (such as dimerization).

The modified XDI having the functional group (h) (uretonimine group) can be obtained by reacting the XDI composition to form a carbodiimide group in the presence of a known carbodiimide-forming catalyst and then adding XDI to the carbodiimide group.

The modified XDI having the functional group (i) (carbodiimide group) can be obtained by reacting the XDI composition in the presence of a known carbodiimide-forming catalyst.

It should be noted that the modified XDI composition has at least one of the functional groups (a)-(i), or may have two or more. Such modified XDI composition can be produced by using the above reactions in combination appropriately. In addition, the modified XDI composition can be used alone or in a combination of two or more.

A fourth object of the present application is to provide a two-component polyurethane raw material, and the two-component polyurethane raw material includes agent A and agent B;

the agent A includes the xylylene diisocyanate composition according to the first object and/or the modified composition according to the third object; and the agent B includes a substance having an active hydrogen group.

The two-liquid resin raw material, which contains the isocyanate component containing the XDI composition and/or the modified XDI composition as the agent A and the component containing an active hydrogen group as the agent B, is suitably applied to, for example, a coating raw material such as coatings and adhesives, a two-component curing sealing raw material, a potting agent, etc. Such two-component resin raw material is a raw material which needs to combine the agent A (curing agent) and the agent B (main agent) prepared separately before use.

The coating raw material is a two-component curing resin raw material used to form a coating layer, containing the agent A (curing agent) and the agent B (main agent). The coating layer may contain coatings, adhesives, etc.

When the coating raw material is used as coatings, examples of coatings include coatings for plastics, coatings for automotive exterior decorations, coatings for automotive interior decorations, coatings for electrical/electronic materials, coatings for optical materials (such as lenses), coatings for building materials, coatings for glass coating layer, coatings for carpentry, coatings for film coating, coatings for inks, coatings for artificial leathers (coating layer agents), lacquers (coating layer agents), etc.

As a polyisocyanate component, the agent A may contain, for example, the modified XDI composition (hereinafter, denoted as the modified XDI composition for coating), and preferably contain: a modified XDI composition having the functional group (a) (isocyanurate group), and/or a modified XDI composition having the functional group (d) (carbamate group). In addition, the agent A can contain other aromatic isocyanates, aliphatic isocyanates, and aromatic aliphatic isocyanates, as needed.

A containing proportion of IBA in the XDI composition which is modified to prepared the modified XDI composition is more than or equal to 0.2 ppm and less than or equal to 500 ppm.

If the containing proportion of IBA in the XDI composition for coating is within the above range, the coating material can be inhibited in color changing.

As a component having an active hydrogen group, the agent B may contain, for example, the high molecular mass polyol. The high molecular mass polyol used as a coating material (hereinafter, denoted as the high molecular mass polyol for coating) may be, for example, the acrylic acid-based polyol, the polyester polyol, and the fluorine polyol.

In addition, as needed, the agent B may include a carbamate-forming catalyst, an anti-hydrolysis agent, a defoamer, a surfactant, a sliding imparter, a surface conditioner, an antioxidant, a weather stabilizer, a colorant, a dye, a filler and resin powders according to appropriate proportions.

As a method for forming a coating material, for example, the agent A and the agent B are mixed, and the mixture is coated on the coating object via a known method and cured.

As a result, the coating material can be formed. Such coating material has excellent color-changing resistance.

The color difference (Δb) of the coating layer in the damp and hot resistance test (2000 hours) is, for example, more than or equal to 0.5, and, for example, less than or equal to 2.4, preferably less than or equal to 2.2, more preferably less than or equal to 2.0, and further preferably less than or equal to 1.9.

A fifth object of the present application is to provide a polyurethane resin, and the polyurethane resin is obtained by reacting the xylylene diisocyanate composition according to the first object with a substance having an active hydrogen group, or by reacting the modified composition according to the third object with a substance having an active hydrogen group.

The substance containing an active hydrogen group may be, for example, a polyol component (component mainly containing polyol having two or more hydroxyl groups), a polythiol component (component mainly containing polythiol having two or more mercapto groups (thiol groups)), a polyamine component (component mainly containing polyamine having two or more amino groups), etc.

The polyol component may be, for example, a low molecular mass polyol and a high molecular mass polyol.

The low molecular mass polyol is a compound having two or more hydroxyl groups with a number-average molecular mass of more than or equal to 60 and less than or equal to 400.

The low molecular mass polyol may be, for example, dihydric alcohol such as ethylene glycol, propylene glycol, 1,3-propanediol, 1,4-butanediol, 1,3-butanediol, 1,2-butanediol, 1,5-pentanediol, 1,6-hexanediol, neopentyl glycol, alkane(7-22)diol, diethylene glycol, triethylene glycol, dipropylene glycol, 3-methyl-1,5-pentanediol, alkyl-1,2-diol (C (carbon number, similarly in the following.) 17-20), isosorbide, 1,3- or 1,4-cyclohexanedimethanol and a mixture thereof, 1,4-cyclohexanediol, hydrogenated bisphenol A, 1,4-dihydroxy-2-butene, 2,6-dimethyl-1-octene-3,8-diol and bisphenol A, trihydric alcohol such as glycerol and trimethylolpropane, tetrahydric alcohol such as tetramethylolmethane (pentaerythritol) and diglycerol, pentahydric alcohol such as xylitol, hexahydric alcohol such as sorbitol, mannitol, allitol, iditol, euonymol, altritol, inositol, dipentaerythritol, seven-membered alcohol such as persitol, and eight-membered alcohol such as sucrose, etc.

In addition, polyepoxide, which is obtained by subjecting alkylene oxide such as ethylene oxide and propylene oxide to addition with the polyol as an initiator and has a number average molecular mass of more than or equal to 60 and less than or equal to 400 (random and/or block copolymer containing two or more alkylene oxide), also belongs to the low molecular mass polyol.

The high molecular mass polyol is a compound having two or more hydroxyl groups with a number average molecular mass of more than or equal to 400 and, for example, less than or equal to 10000, preferably less than or equal to 5000. The high molecular mass polyol may be, for example, polyether polyol, polyester polyol, polycarbonate polyol, polyurethane polyol, epoxy polyol, vegetable oil polyol, polyolefin polyol, acrylic acid-based polyol, polysiloxane polyol, fluorine polyol, and vinyl monomer-modified polyol.

The polyether polyol may be, for example, polyoxy(C2-C3)alkylidene polyol, polytetramethylene ether glycol, polytrimethylene ether glycol, etc. The polyoxy(C2-C3) alkyl-idene polyol may be, for example, a polymer from the addition of C2-3 alkylene oxide such as ethylene oxide and propylene oxide with the low molecular mass polyol as an initiator (random and/or block copolymer containing two or more alkylene oxide). In addition, the polyoxy(C2-3) alkylidene may specifically be, for example, polyethylene glycol, polypropylene glycol, polyethylene polypropylene copolymer, etc.

The polytetramethylene ether glycol may be, for example, a ring-opening polymer (polytetramethylene ether glycol) obtained from cationic polymerization of tetrahydrofuran, and amorphous polytetramethylene ether glycol obtained from copolymerization of tetrahydrofuran polymerization unit and the dihydric alcohol.

In addition, polytetramethylene ether glycol can also be those from plants which are based on the tetrahydrofuran from a plant raw material such as furfural as a starting material.

The polytrimethylene ether glycol may be, for example, polyol prepared from condensation of 1,3-propanediol from plants.

The polyester polyol may be, for example, a condensation product obtained by reacting the low molecular mass polyol (preferably dihydric alcohol) with polyacid (preferably binary acid) under known conditions.

The polyacid may be, for example, saturated aliphatic dicarboxylic acid (C11-C13) such as oxalic acid, malonic acid, succinic acid, methylsuccinic acid, glutaric acid, adipic acid, 1,1-dimethyl-1,3-dicarboxypropane, 3-methyl-3-ethyl glutaric acid, azelaic acid, sebacic acid, unsaturated aliphatic dicarboxylic acid such as maleic acid, fumaric acid and itaconic acid, aromatic dicarboxylic acid such as phthalic acid, isophthalic acid, terephthalic acid, toluene dicarboxylic acid and naphthalene dicarboxylic acid, alicyclic dicarboxylic acid such as hexahydrophthalic acid, and other carboxylic acid such as dimeric acid, hydrogenated dimeric acid, HET acid, and anhydride derived from these carboxylic acids such as oxalic anhydride, succinic anhydride, maleic anhydride, phthalic anhydride, 2-alkyl (C12-C18) succinic anhydride, tetrahydrophthalic anhydride and trimellitic anhydride, and acyl halide derived from these carboxylic acids such as oxalyl dichloride, hexanedioyl dichloride, decanedioyl dichloride, etc.

In addition, the polyester polyol may be, for example, vegetable oil-based polyester polyol obtained from condensation reaction of the low molecular mass polyol and hydroxy carboxylic acid such as vegetable oil fatty acid having hydroxyl groups (such as castor oil fatty acid containing ricinoleic acid and hydrogenated castor oil fatty acid containing 12-hydroxystearic acid) under known conditions.

In addition, the polyester polyol may be, for example, lactone-based polyester polyol obtained from copolymerization of polycaprolactone polyol and polyvalerolactone polyol, which are obtained from ring-opening polymerization of lactones such as ε-caprolactone and γ-valerolactone, and the dihydric alcohol with the low molecular mass polyol (preferably dihydric alcohol) as an initiator.

The polycarbonate polyol may be, for example, amorphous polycarbonate polyol obtained from copolymerization of the dihydric alcohol and a ring-opening polymer of ethylene carbonate which uses the low molecular mass polyol (preferably dihydric alcohol) as an initiator.

In addition, the polyurethane polyol may be, for example, polyester polyurethane polyol, polyether polyurethane polyol, polycarbonate polyurethane polyol, or polyester polyether polyurethane polyol, which are obtained by reacting the polyisocyanate (including XDI; it is also applicable hereinafter) with the polyester polyol, polyether polyol and/or polycarbonate polyol via the above methods wherein an equivalent ratio of the hydroxyl group to isocyanate group (OH/NCO) is greater than 1.

The epoxy polyol may be, for example, those obtained by reacting the low molecular mass polyol with polyfunctional halogenated alcohol such as epichlorohydrin and P-methyl epichlorohydrin.

The vegetable oil polyol may be, for example, vegetable oil having hydroxyl groups, such as castor oil and coconut oil. For example, it may be castor oil polyol, or ester-modified castor oil polyol obtained by reacting castor oil polyol with polypropylene polyol.

The polyolefin polyol may be, for example, polybutadiene polyol, and partially saponified ethylene-vinyl acetate copolymer, etc.

The acrylic acid-based polyol may be, for example, a copolymer obtained from copolymerization of acrylate having a hydroxyl group and the copolymerizable vinyl monomer which can be copolymerized with the acrylate having a hydroxyl group.

The acrylate having a hydroxyl group may be, for example, 2-hydroxyethyl (methyl)acrylate, hydroxypropyl (methyl)acrylate, hydroxybutyl (methyl)acrylate, 2,2-dihydroxymethylbutyl (methyl)acrylate, polyhydroxyalkyl maleate, polyhydroxyalkyl fumarate, etc. Preferably, it may be 2-hydroxyethyl (methyl)acrylate.

The copolymerizable vinyl monomers may be, for example, alkyl (methyl)acrylate (carbon number 1-12) such as methyl (methyl)acrylate, ethyl (methyl)acrylate, propyl (methyl)acrylate, isopropyl (methyl)acrylate, butyl (methyl) acrylate, isobutyl (methyl)acrylate, sec-butyl (methyl)acrylate, tert-butyl (methyl)acrylate, pentyl (methyl)acrylate, isopentyl (methyl)acrylate, hexyl (methyl)acrylate, isononyl (methyl)acrylate, 2-ethylhexyl (methyl)acrylate, cyclohexyl (methyl)acrylate and isobornyl (methyl)acrylate; and for example, styrene, vinyl toluene, a-methyl styrene, etc.

Aromatic vinyl monomers, vinyl cyanide such as (methyl) acrylonitrile, vinyl monomers having a carboxyl group such as (methyl)acrylic acid, fumaric acid, maleic acid, itaconic acid, or their alkyl esters, alkyl polyol poly(methyl)acrylate such as ethylene glycol di(methyl)acrylate, butylene glycol di(methyl)acrylate, hexylene glycol di(methyl)acrylate, oligo-ethylene glycol di(methyl)acrylate, trimethylol propane di(methyl)acrylate, and trimethylol propane tris(methyl)acrylate, and vinyl monomers containing an isocyanate group such as 3-(2-isocyanato-2-propyl)-α-methyl styrene, etc.

In addition, the acrylic acid-based polyol can be obtained from copolymerization of those acrylate having a hydroxyl group and the copolymerizable vinyl monomer in the presence of a suitable solvent and a polymerization initiator.

In addition, the acrylic acid-based polyol includes, for example, polysiloxane polyol and fluorine polyol.

The polysiloxane polyol may be, for example, an acrylic acid-based polyol obtained from copolymerization of the acrylic acid-based polyol and a polysiloxane compound having a vinyl group as a copolymerizable vinyl monomer, such as γ-methacryloxy propyl trimethoxysilane.

The fluorine polyol may be, for example, an acrylic acid-based polyol obtained from copolymerization of the acrylic acid-based polyol and a fluorine compound having a vinyl group as a copolymerizable vinyl monomer, such as tetrafluoroethylene and chlorotrifluoroethylene.

The vinyl monomer-modified polyol can be obtained by reacting the high molecular mass polyol with the vinyl monomer such as the alkyl (methyl)acrylate.

The polyol component can be used alone or in a combination of two or more.

In addition, in the reaction of the polyisocyanate component and the component having an active hydrogen group, an isocyanate-ended polymer having an isocyanate group at the end of the molecule will be produced when the equivalent ratio of the active hydrogen group to the isocyanate group is less than 1, and an active hydrogen-ended polymer having an active hydrogen group at the end of the molecule will be produced when the equivalent ratio of the active hydrogen group to the isocyanate group is greater than 1. Both the isocyanate-ended polymer and the active hydrogen group-ended polymer are included in the resin (polyurethane resin). The isocyanate-ended polymer is a one-component curing resin.

As use of the polyurethane resin, specifically, the polyurethane resin can be suitably applied to inks, transfer foils, binding agents, binders, gels, elastomers, foams, adhesives, liquid curing sealing materials, RIM moldings, microfoam polyurethanes, various microcapsules, optical materials, aqueous resins, thermosetting resins, active energy ray (such as electron beam and ultraviolet ray, etc.) curable resins, artificial and synthetic leathers, solidifying powders, robot components, mobile components, health care materials, carbon fiber reinforced plastic (CFRP) base resins, transparent rubber, transparent hard resins, waterproof materials, films, sheets, tubes, plates, speakers, sensors, organic electroluminescent components, solar power generation components, robot components, wearable components, sports goods, leisure goods, medical goods, nursing care goods, housing components, audio components, lighting components, chandeliers, exterior lights, packaging, vibration-proof/anti-vibration/shock-absorbing components, sound-proof components, daily necessities, sundry goods, buffers, bedding, stress-absorbing materials, stress-relieving materials, interior and exterior decorations for automobiles, conveyor components, components for office automation equipment, surface protection components for general merchandise, self-healing materials, health equipment, etc.

A sixth object of the present application is to provide an elastomer material, and the elastomer material includes the polyurethane resin according to the fifth object.

The elastomer may be, for example, thermoplastic polyurethane elastomer (TPU), thermosetting polyurethane elastomer (TSU), rolling-type polyurethane elastomer, etc.

The elastomer includes soft chains and hard chains, the soft chains are formed by reacting XDI with a high molecular mass polyol, and the hard chains are formed by reacting XDI with a low molecular mass polyol and/or a low molecular mass polyamine.

Such elastomer can be prepared from, for example, reaction of a polyisocyanate component, a high molecular mass polyol (component having an active hydrogen group) and a low molecular mass polyol and/or a low molecular mass polyamine (component having an active hydrogen group). In other words, the polyisocyanate component, high molecular mass polyol and low molecular mass polyol and/or low molecular mass polyamine are elastomer raw materials.

As the elastomer raw material, the high molecular mass polyol may be, for example, the polyester polyol (such as polycaprolactone polyol, and adipic acid-based polyester polyol (polyester polyol using adipic acid as a polyacid)), the polycarbonate polyol, the polytetramethylene ether glycol (such as polytetramethylene ether glycol), and preferably adipic acid-based polyester polyol.

As the elastomer raw material, the low molecular mass polyol may be, for example, ethylene glycol, 1,4-butanediol, and preferably 1,4-butanediol.

As the elastomer raw material, the low molecular mass polyamine may be, for example, the low molecular mass polyamine as described above.

The elastomer can be prepared via, for example, known methods such as a one-step method or a prepolymer method.

It should be noted that the preparation method for the elastomer can be, for example, bulk polymerization, solution polymerization, etc.

In addition, in the preparation method for the elastomer, the known carbamate-forming catalyst such as amines and organometallic compounds (such as an organotin compound, and preferably dibutyltin dichloride) can be added to the elastomer raw material as needed. Furthermore, as needed, the elastomer may include a plasticizer, an anti-caking agent, a heat stabilizer, a light stabilizer, an ultraviolet absorber, an anti-yellowing agent, an antioxidant, a release agent, a colorant, a dye, a lubricant, a nucleating agent, a filler and an anti-hydrolysis agent according to appropriate proportions.

As a result, the elastomer can be prepared. Such elastomer not only inhibits the white cloudiness and has excellent color-changing resistance, but also has excellent mechanical properties (elongation and strength).

The color difference ($\Delta b$) of the elastomer in the xenon-lamp irradiation test (240 hours) is, for example, more than or equal to 1.0, and, for example, less than or equal to 3.9, preferably less than or equal to 3.5, more preferably less than or equal to 3.0. The color difference of the elastomer in the xenon-lamp irradiation test can be determined according to a method documented in an example as described later.

A seventh object of the present application is to provide an optical material, and the optical material is obtained by polymerizing the xylylene diisocyanate composition according to the first object with a polythiol compound, or by polymerizing the modified composition according to the third object with a polythiol compound.

In the present application, the polythiol compound refers to a compound having at least two thiol groups.

Preferably, the optical materials include a plastic lens material, a vehicle lampshade material, a transparent roof material, or a lens material for smartphones or tablets.

Preferably, the polythiol compound is selected from methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, bis(2-mercaptoethyl) thiomalate, 2,3-dimercapto-1-propanol(2-mercaptoacetate), 2,3-dimercapto-1-propanol(3-mercapto propionate), diglycol bis(2-mercaptoacetate), diglycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl)ether, ethylene glycol bis(2-mercaptoacetate), ethylene glycol bis(3-mercaptopropionate), trimethylolpropane bis(2-mercaptoacetate), trimethylolpropane bis(3-mercaptopropionate), pentaerythritol tetra(2-mercaptoacetate), pentaerythritol tetra(3-mercaptopropionate), tetra(mercaptomethyl) methane, and other aliphatic polythiol compounds;

1,2-benzenedithiol, 1,3-benzenedithiol, 1,4-benzenedithiol, 1,2-bis(mercaptomethyl)benzene, 1,3-bis(mercaptomethyl)benzene, 1,4-bis(mercaptomethyl)benzene, 1,2-bis(mercaptoethyl) benzene, 1,3-bis(mercaptoethyl)benzene, 1,4-bis(mercaptoethyl) benzene, 1,2,3-trimercapto benzene, 1,2,4-trimercaptobenzene, 1,3,5-trimercaptobenzene, 1,2,3-tris(mercaptomethyl) benzene, 1,2,4-tris(mercaptomethyl)benzene, 1,3,5-tris(mercaptomethyl) benzene, 1,2,3-tris (mercaptoethyl)benzene, 1,2,4-tris(mercaptoethyl)benzene, 1,3,5-tris(mercaptoethyl) benzene, toluene-2,5-dithiol, toluene-3,4-dithiol, 1,3-bis(p-methoxyphenyl)propane-2,2-dithiol, 1,3-diphenylpropane-2,2-dithiol, phenylmethane-1,1-dithiol, 2,4-bis(p-mercaptophenyl)pentane, and other aromatic polythiol compounds;

1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris (mercaptoethylthio)benzene, 1,3,5-tris(mercaptoethylthio)benzene, and their alkylates, and aromatic polythiol compounds having a sulfur atom in addition to the mercapto groups;

bis(mercaptomethyl) sulfide, bis(mercaptomethyl) disulfide, bis(mercaptoethyl) sulfide, bis(mercaptoethyl) disulfide, bis(mercaptopropyl) sulfide, bis(mercaptomethylthio)methane, bis(2-mercaptoethylthio)methane, bis(3-mercaptopropanethiol)methane, 1,2-bis(mercapto methylthio)ethane, 1,2-bis(2-mercaptoethylthio) ethane, 1,2-bis(3-mercaptopropyl)ethane, 1,3-bis(mercaptomethylthio)propane, 1,3-bis(2-mercaptoethylthio)propane, 1,3-bis(3-mercapto propanethiol)propane, 1,2,3-tris(mercaptomethylthio) propane, 1,2,3-tris(2-mercaptoethylthio) propane, 1,2,3-tris(3-mercaptopropanethiol)propane, 1,2-bis[(2-mercaptoethyl)thio]-3-mercaptopropane, 4,8-dimercaptomethyl-1,11-dimercapto-3,6,9-trithiaundecane, 4,7-dimercapto methyl-1,11-dimercapto-3,6,9-trithiaundecane, 5,7-dimercaptomethyl-1,11-dimercapto-3,6,9-tri thiaundecane, bis(mercaptomethyl)-3,6,9-trithia-1,11-undecanedithiol, tetra(mercaptomethyl thiomethyl) methane, tetra(2-mercaptoethylthiomethyl)methane, tetra(3-mercaptopropane thiomethyl)methane, bis(2,3-dimercaptopropyl)sulfide, bis(1,3-dimercaptopropyl) sulfide, 2,5-dimercapto-1,4-dithiane, 2,5-dimercaptomethyl-1,4-dithiane, 2,5-dimercaptomethyl-2,5-dimethyl-1,4-dithiane, bis(mercaptomethyl) disulfide, bis(mercaptoethyl) disulfide, bis(mercaptopropyl) disulfide, and other aliphatic polythiol compounds having a sulfur atom in addition to the mercapto groups, and their esters of mercaptoacetic acid and mercaptopropionic acid;

hydroxymethyl sulfide bis(2-mercaptoacetate), hydroxymethyl sulfide bis(3-mercapto propionate), hydroxyethyl sulfide bis(2-mercaptoacetate), hydroxyethyl sulfide bis(3-mercapto propionate), hydroxypropyl sulfide bis(2-mercaptoacetate), hydroxypropyl sulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercapto acetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), thiodiglycolic acid bis(2-mercaptoacetate), thiodipropionic acid bis(2-mercaptoacetate), 4,4-thiodibutyric acid bis(2-mercaptoacetate), dithiodiglycollic acid bis(2-mercaptoacetate), dithiodipropionic acid bis(2-mercaptoacetate), 4,4-dithiodibutyric acid bis(2-mercaptoacetate), thiodiglycolic acid bis(2,3-dimercaptopropyl), thiodipropionic acid bis(2,3-dimercaptopropyl), dithiodiglycollic acid bis(2,3-dimercaptopropyl), dithiodipropionate acid bis(2,3-dimercaptopropyl), and other aliphatic polythiol compounds having a sulfur atom and an ester bond in addition to mercapto groups;

3,4-thiophenedithiol, 2,5-dimercapto-1,3,4-thiadiazole, and other heterocyclic compounds having a sulfur atom in addition to mercapto groups;

2-mercaptoethanol, 3-mercapto-1,2-propanediol, glycerol di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tri (3-mercaptopropionate), pentaerythritol mono (3-mercaptopropionate), pentaerythritol bis(3-mercaptopropionate), pentaerythritol tri(mercapto acetate), dipentaerythritol penta(3-mercaptopropionate), hydroxymethyl-tris(mercaptoethylthiomethyl) methane, 1-hydroxyethylthio-3-mercaptoethylthiobenzene, and other compounds having a hydroxyl group in addition to mercapto groups;

1,1,3,3-tetra(mercaptomethylthio)propane, 1,1,2,2-tetra (mercaptomethylthio)ethane, 4,6-bis(mercaptomethylthio)-1,3-dithiane, 1,1,5,5-tetra(mercaptomethylthio)-3-thiopentane, 1,1,6,6-tetra(mercaptomethylthio)-3,4-dithiohexane, 2,2-bis(mercaptomethylthio)ethanethiol, 2-(4,5-dimercapto-2-thiopentyl)-1,3-dithiolane, 2,2-bis (mercaptomethyl)-1,3-dithiolane, 2,5-bis(4,4-bis(mercaptomethylthio)-2-thiobutyl)-1,4-dithiane, 2,2-bis (mercapto methylthio)-1,3-propanedithiol, 3-mercaptomethylthio-1,7-dimercapto-2,6-dithioheptane, 3,6-bis(mercaptomethylthio)-1,9-dimercapto-2,5,8-trithianonane, 4,6-bis (mercaptomethylthio)-1,9-dimercapto-2,5,8-trithianonane, 3-mercaptomethylthio-1,6-dimercapto-2,5-dithiohexane, 2-(2,2-bis (mercaptomethylthio)ethyl)-1,3-dithietane 1,1,9,9-tetra (mercaptomethylthio)-5-(3,3-bis (mercaptomethylthio)-1-thiopropyl)3,7-dithianonane, tris(2,2-bis(mercaptomethylthio)ethyl)methane, tris(4,4-bis(mercaptomethylthio)-2-thiobutyl)methane, tetra (2,2-bis(mercaptomethylthio)ethyl)methane, tetra(4,4-bis(mercapto methylthio)-2-thiobutyl)methane, 3,5,9,11-tetra(mercaptomethylthio)-1,13-dimercapto-2,6,8,12-tetrathiatridecane, 3,5,9,11,15,17-hexa (mercaptomethylthio)-1,19-dimercapto-2,6,8,12,14,18-hexathianonadecane, 9-(2,2-bis (mercaptomethylthio)ethyl)-3,5,13,15-tetra (mercaptomethylthio)-1,17-dimercapto-2,6,8,10,12,16-hexathiaheptadecane, 3,4,8,9-tetra (mercaptomethylthio)-1,11-dimercapto-2,5,7,10-tetrathiaundecane, 3,4,8,9,13,14-hexa(mercaptomethylthio)-1,16-dimercapto-2,5,7,10,12,15-hexathiahexadecane, 8-{bis (mercapto methylthio)methyl}-3,4,12,13-tetra(mercaptomethylthio)-1,15-dimercapto-2,5,7,9,11,14-hexathiapentadecane, 4,6-bis{3,5-bis (mercaptomethylthio)-7-mercapto-2,6-dithioheptylthio}-1,3-dithiane, 4-{3,5-bis (mercaptomethylthio)-7-mercapto-2,6-dithioheptylthio}-6-mercaptomethyl thio-1,3-dithiane, 1,1-bis{4-(6-mercaptomethylthio)-1,3-dithiane-yl-thio}-3,3-bis(mercapto methylthio)propane, 1,3-bis{4-(6-mercaptomethylthio)-1,3-dithiane-yl-thio}-1,3-bis (mercapto methylthio)propane, 1-{4-(6-mercaptomethylthio)-1,3-dithiane-yl-thio}-3-{2,2-bis (mercapto methylthio)ethyl}-7,9-bis (mercaptomethylthio)-2,4,6,10-tetrathiaundecane, 1-{4-(6-mercapto methylthio)-1,3-dithiane-yl-thio}-3-{2-(1,3-dithietane-yl)}methyl-7,9-bis(mercaptomethylthio)-2,4,6,10-tetrathiaundecane, 1,5-bis{4-(6-mercaptomethylthio)-1,3-dithiane-yl-thio}-3-{2-(1,3-dithietane-yl)}methyl-2,4-dithiolane, 4,6-bis[3-{2-(1,3-dithietane-yl)}methyl-5-mercapto-2,4-dithiapentanylthio]-1,3-dithiane, 4,6-bis{4-(6-mercaptomethylthio)-1,3-dithiane-yl-thio}-1,3-dithiane, 4-{4-(6-mercaptomethylthio)-1,3-dithiane-yl-thio}-6-{4-(6-mercaptomethylthio)-1,3-dithiane-yl-thio}-1,3-dithiane, 3-{2-(1,3-dithietane-yl)}methyl-7,9-bis(mercaptomethylthio)-1,11-dimercapto-2,4,6,10-tetrathiaundecane, 9-{2-(1,3-dithietane-yl)}methyl-3,5,13,15-tetra(mercaptomethylthio)-1,17-dimercapto-2,6,8,10,12,16-hexathiaheptadecane, 3-{2-(1,3-dithietane-yl)}methyl-7,9,13,15-tetra (mercaptomethylthio)-1,17-dimercapto-2,4,6,10,12,16-hexathiaheptadecane, 3,7-bis{2-(1,3-dithietane-yl)}methyl-1,9-dimercapto-2,4,6,8-tetrathianonane, 4-{3,4,8,9-tetra(mercaptomethylthio)-11-mercapto-2,5,7,10-tetrathiaundecyl}-5-mercaptomethylthio-1,3-dithiolane, 4,5-bis{3,4-bis(mercaptomethylthio)-6-mercapto-2,5-dithiohexylthio}-1,3-dithiolane, 4-{3,4-bis (mercaptomethylthio)-6-mercapto-2,5-dithiohexylthio}-5-mercaptomethylthio-1,3-dithiolane, 4-{3-bis(mercaptomethylthio)methyl-5,6-bis(mercaptomethylthio)-8-mercapto-2,4,7-trithiooctyl}-5-mercaptomethylthio-1,3-dithiolane, 2-[bis{3,4-bis(mercaptomethylthio)-6-mercapto-2,5-dithiohexylthio}methyl]-1,3-dithietane, 2-{3,4-bis (mercaptomethylthio)-6-mercapto-2,5-dithiohexylthio}mercaptomethylthiomethyl-1,3-dithietane, 2-{3,4,8,9-tetra(mercaptomethylthio)-11-mercapto-2,5,7,10-tetrathiaundecylthio}mercaptomethylthiomethyl-1,3-dithietane, 2-{3-bis(mercaptomethylthio)methyl-5,6-bis(mercaptomethylthio)-8-mercapto-2,4,7-trithiooctyl}mercaptomethylthiomethyl-1,3-dithietane, 4,5-bis[1-{2-(1,3-dithietane-yl)}-3-mercapto-2-thiapropanethio]-1,3-dithiolane, 4-[1-{2-(1,3-dithietane-yl)}-3-mercapto-2-thiapropanethio]-5-{1,2-bis(mercapto methylthio)-4-mercapto-3-thiabutylthio}-1,3-dithiolane, 2-[bis{4-(5-mercaptomethylthio-1,3-dithiolane-yl)thio}]methyl-1,3-dithietane, 4-{4-(5- mercaptomethylthio-1,3-dithiolane-yl)thio}-5-[1-{2-(1,3-dithietane-yl)}-3-mercapto-2-thiapropanethio]-1,3-dithiolane, etc., and their oligomers, which have a dithioacetal or dithioketal structure;

tris(mercaptomethylthio)methane, tris(mercaptoethylthio)methane, 1,1,5,5-tetra(mercapto methylthio)-2,4-dithiolane, bis(4,4-bis(mercaptomethylthio)-1,3-dithiobutyl) (mercapto methylthio)methane, tris(4,4-bis (mercaptomethylthio)-1,3-dithiobutyl)methane, 2,4,6-tris(mercaptomethylthio)-1,3,5-trithiane, 2,4-bis (mercaptomethylthio)-1,3,5-trithiane, 1,1,3,3-tetra (mercaptomethylthio)-2-thiopropane, bis (mercaptomethyl)methylthio-1,3,5-trithiane, tris((4-mercaptomethyl-2,5-dithiane-1-yl)methylthio) methane, 2,4-bis(mercaptomethylthio)-1,3-dithiolane, 2-mercaptoethylthio-4-mercaptomethyl-1,3-dithiolane, 2-(2,3-dimercaptopropanethio)-1,3-dithiolane, 4-mercaptomethyl-2-(2,3-dimercaptopropanethio)-1,3-dithiolane, 4-mercaptomethyl-2-(1,3-dimercapto-2-propanethio)-1,3-dithiolane, tris(2,2-bis(mercapto methylthio)-1-thioethyl)methane, tris(3,3-bis(mercaptomethylthio)-2-thiopropyl)methane, tris(4,4-bis(mercaptomethylthio)-3-thiobutyl)methane, 2,4,6-tris(3,3-bis(mercaptomethyl thio)-2-thiopropyl)-1,3,5-trithiane, tetra(3,3-bis(mercaptomethylthio)-2-thiopropyl)methane, etc., and their oligomers, which have a trithioorthoformate structure;

3,3'-bis(mercaptomethylthio)-1,5-dimercapto-2,4-dithiolane, 2,2'-bis(mercaptomethylthio)-1,3-dithiolane, 2,7-bis(mercaptomethyl)-1,4,5,9-tetrathiaspiro[4,4] nonane, 3,9-dimercapto-1,5,7,11-tetrathiaspiro[5,5]undecane, and their oligomers, which have a tetrathioorthocarbonate structure.

However, the polythiol compound is not limited to the compounds listed above. In addition, the compounds listed above can be used alone or in a combination of two or more.

Among the compounds listed above, the polythiol compound is preferably selected from at least one of 1,2-bis[(2-mercaptoethyl)thio]-3-mercaptopropane, bis(mercaptomethyl)-3,6,9-trithia-1,11-undecanedithiol, pentaerythritol tetra(3-mercaptopropionate), 1,1,3,3-tetra (mercaptomethylthio)propane and 2-mercaptoethanol.

Preferably, a preparation method for the optical material is carried out in the presence of a polymerization catalyst, and the polymerization catalyst is preferably an organotin compound, and for example, dialkyltin halides such as dibutyltin dichloride and dimethyltin dichloride, or dialkyltin dicarboxylate such as dimethyltin diacetate, dibutyltin dioctanoate and dibutyltin dilaurate.

In addition, in the preparation method for the optical material, various additives are optionally added as needed, such as a chain extender, a crosslinker, a light stabilizer, a ultraviolet absorber, an antioxidant, an oil-soluble dye, a filler, a release agent, etc.

Optical materials made of polyurethane resin are typically prepared using injection molding-polymerization. Specifically, a polythiol compound and an isocyanate compound are mixed, and optionally added with a suitable additive. This mixture (polymeric composition) is degassed, if necessary, by an appropriate method, then injected into an injection mold for optical materials, and then, usually, slowly heated from low temperature to high temperature to polymerize. Then, the optical material is obtained after released from the mold.

If the containing proportion of IBA in the XDI composition or the modified XDI composition is more than or equal to 0.2 ppm and less than or equal to 500 ppm, the XDI composition or the modified XDI composition for optical materials can be stably prepared into optical materials. If the containing proportion of IBA in the XDI composition or the modified XDI composition is less than or equal to the upper limitation, the optical material can be inhibited in color changing.

The yellowness index YI of the optical material provided in the present application can be controlled less than or equal to 1.7 and as low as 1.5.

Compared with the prior art, the present application has the beneficial effects below.

The xylylene diisocyanate composition provided in the present application contains 0.2-500 ppm of the compound as shown in formula (1), the resin prepared from it has excellent color-changing resistance, and the resin is effectively inhibited in yellowing and/or white cloudiness.

Other aspects can be understood upon reading and understanding the detailed description.

BRIEF DESCRIPTION OF DRAWINGS

FIG. 1 is an equipment flow chart of preparing a xylylene diisocyanate composition in an embodiment of the present application;

1—salt-forming reactor, 2—first phosgenation reactor, 3—second phosgenation reactor, 4—third phosgenation reactor, 5—phosgene removal column, 6—solvent removal column, 7—tar removal device, 8—rectification column, and 9—solvent refining column.

DETAILED DESCRIPTION

(I) Determination Methods for Relevant Tests in the Present Application are as Follows 1. Containing Proportion of Compound IBA Firstly, the IBA with a purity of 99 mol % synthesized as described below is used as a standard substance and analyzed by gas chromatography under the following conditions, and a standard curve is established based on the area value of the obtained gas chromatogram (external standard method).

Analytical instrument: Agilent 5977B GCMS;

column: DB-5 (30 m×0.25 mm×0.25 m);

column chamber temperature: the temperature is held at 50° C. for 2 min, raised up to 80° C. at 5 mL/min, then raised up to 280° C. at 15 mL/min, and held for 10 min;

split ratio: no split;

inlet temperature: 280° C.;

detection temperature: 300° C.;

carrier gas: helium;

carrier gas flow rate: 1 mL/min (constant flow rate);

injection volume: 1 μL; and detection method: SIM selected ion scanning mode (161, 132).

2. Containing Proportion of Xylylene Diisocyanate

The XDI with a purity of 99 mol % in an example as described later is used as a standard substance and analyzed by gas chromatography under the following conditions using the internal standard method.

Instrument: Agilent 7890

(1) column: DB-5 (30 m×0.25 mm×0.25 m); (2) injection volume: 0.5 μL; (3) split ratio: 1/30; (4) inlet temperature: 260° C.; (5) column flow rate: 1.5 mL/min; (6) temperature programming: the temperature is held at 100° C. for 1 min, raised up to 280° C. at 10° C./min and held for 20 min; (7) FID detector temperature: 280° C.; and (8) hydrogen flow rate: 40 mL/min, air flow rate: 400 mL/min.

3. Elemental Bromine Content in XDI Which is Determined and Analyzed by ICP-OES;

Instrument: Thermo Scientific ICAP 7200 ICP-OES

4. Moisture Content of Reuse Solvent Which is Determined by Karl Fischer Moisture Meter;

Instrument: Swiss Metrohm 915 KF Ti-Touch

5. Calculation for Yellowness Index (Y.I.) of Optical Material

The yellowness index of the lens is determined with reference to the China national standard GB/T-2409-1980.

The optical materials of examples and comparative examples as described later are prepared into circular flat plastic lenses with a thickness of 9 mm and a diameter of 75 mm, and tristimulus values x, y, and z are determined by using a spectrophotometer. The Y.I. is calculated using the following equation.

$$YI = \frac{100\times(1.28X - 1.06Z)}{Y}$$

It should be noted that there exists the following relation: the smaller the Y.I., the better the color quality of the plastic lens; the larger the Y.I., the worse the color quality.

6. Weather Resistance Test of Elastomer

Subsequently, the elastomers of examples and comparative examples as described later are subjected to injection molding by using an injection molding machine (Model: NEX-140, Taifu Machinery), wherein a screw speed is 100 rpm, a barrel temperature is 150-235° C., a mold temperature is 20° C., an injection time is 10 seconds, an injection speed is 60 mm/s and a cooling time is 45 seconds.

The obtained sheets (with a thickness of 2 mm) are maintained for 7 days under a constant temperature and humidity condition at 23° C. and 55% relative humidity to obtain elastomer sheets of examples and comparative examples as described later.

Moreover, the b-value (b1, initial value) of the elastomer sheets is determined using a color meter, and then a xenon-lamp irradiation test is performed. After 240 hours, the b-value (b2) of the elastomer sheets is determined as above. The color difference Δb (=|b2−b1|) of the elastomer sheets in the xenon-lamp irradiation test (240 hours) is calculated.

It should be noted that the xenon-lamp irradiation test is performed by using a super Xenon lamp weathering test chamber (WeiBang Instruments) under the conditions that a black panel temperature is 89° C., a relative humidity is 50%, and a xenon lamp irradiance is 100 W/$m^2$ (irradiation wavelength of 300-400 nm).

7. Color Difference (Color Changing and Coloring) of a Coating Layer in Damp and Hot Resistance Test The b-value (b1, initial value) of the polyethylene terephthalate substrates (hereinafter, denoted as the samples) forming the coating layers of examples and comparative examples as described later is determined by using a color difference meter (3nh NR10QC). Subsequently, the samples are maintained in a constant temperature and humidity machine (Gotech Machines) at 85° C. and 85% relative humidity for 2000 hours. The b-value (b2) of the samples after 2000 hours is determined as above. The color difference Δb (=|b2−b1|) of the coating layers in the damp and hot resistance test is calculated.

(II) Preparation of Standard Substance

The IBA as shown in chemical formula (1) is synthesized according to the following synthetic route.

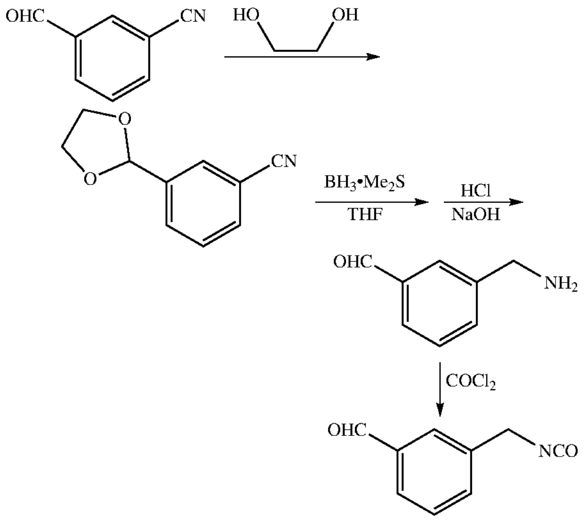

In a 50 mL three-necked flask equipped with a reflux condenser and a manifold, 6.5 g (50 mmol) of 3-cyanobenzaldehyde, 4.35 g (70 mmol) of ethylene glycol, 15 mL of cyclohexane as water-carrying agent and 0.4 g (6% of a mass of 3-cyanobenzaldehyde) of diatomite were added, heated to reflux with stirring for 2 h, cooled, filtered to recover diatomite, and subjected to spin evaporation for cyclohexane removal, and then a colorless aromatic liquid of 3-cyanobenzaldehyde ethylene acetal was obtained which was 7.88 g and had a yield of 90%.

Under the room temperature, 10.1 mL (19.2 mmol) tetrahydrofuran solution of borane-dimethyl sulfide complex was added dropwise to a mixture of 674 mg (3.85 mmol) 3-cyanobenzaldehyde ethylene acetal and 14.0 mL tetrahydrofuran, and then stirred for 23 h for reaction.

After the reaction, 10 mL of water was added dropwise to the reaction solution while cooling it with ice, and then 2.5 mL (5.0 mmol) of 2 M hydrochloric acid was added to the reaction solution and reacted for 2 h. Subsequently, 20 mL of ethyl acetate was added to the reaction solution, and the reaction solution was washed with stirring. The ethyl acetate layer was separated and removed, then the reaction solution was added with 6 mL of 1 M sodium hydroxide and extracted with 15 mL dichloromethane for four times, and the dichloromethane layer obtained was dried with magnesium sulfate. After drying, magnesium sulfate was filtered out from the dichloromethane layer and then dichloromethane was distilled off to obtain 434.0 mg (2.28 mmol) of 3-(aminomethyl)benzaldehyde.

The obtained 3-(aminomethyl)benzaldehyde was analyzed by using $^1$H-NMR (270 MHz, $CDCl_3$).

$^1$H NMR (400 MHz, DMSO) δ 9.88 (s, 1H), 8.69 (b, 2H), 7.65-7.40 (m, 4H), 4.35 (s, 2H).

Subsequently, phosgene was introduced into a mixture of 337.4 mg (1.78 mmol) 3-(amino methyl)benzaldehyde obtained above and 7.0 mL chlorobenzene and then reacted at 120° C., and the reaction was stopped when the reaction solution was clarified. The reaction solution was cooled down to room temperature, the chlorobenzene was distilled off to obtain a concentrate, and 278.0 mg (1.29 mmol) of 3-(isocyanatomethyl)benzaldehyde (IBA) was obtained.

The obtained 3-(isocyanatomethyl)benzaldehyde (IBA) was analyzed by using $^{1}H$-NMR (270 MHz, $CDCl_3$) and $^{13}C$-NMR (100 MHz, $CDCl_3$).

$^{1}H$-NMR (400 MHz, $CDCl_3$) δ 9.86 (s, 1H), 7.65-7.36 (m, 4H), 4.63 (s, 2H).

$^{13}C$-NMR (100 MHz, $CDCl_3$) δ 191.0, 139.4, 139.2, 133.7, 130.1, 129.1, 126.9, 125.0, 54.6.

To understand the present application, examples are listed as follows in the present application. It should be apparent to those skilled in the art that the examples are merely used for a better understanding of the present application and should not be regarded as a specific limitation on the present application.

It should be noted that the terms "parts" and "%" are based on mass unless specified otherwise.

Examples 1-7, Comparative Example 1

Each of the examples and comparative example provides an XDI composition, the specific composition of which is detailed in Table 1.

A preparation method for the XDI composition is as follows.

The XDI composition was prepared according to the process shown in FIG. 1. Specifically, 800 parts by mass of chlorobenzene were loaded into a salt-forming reactor shown in FIG. 1. Subsequently, a salt-forming temperature in the salt-forming reactor was adjusted to 30° C., and a salt-forming pressure (gauge pressure) in the salt-forming reactor was adjusted to 0.05 MPaG. Then, 128 parts by mass of HCl gas were introduced into the salt-forming reactor through a hydrogen chloride feeding pipeline, and a mixture (amine solution) of 150 parts by mass of 1,3-XDA and 1050 parts by mass of chlorobenzene was introduced into the salt-forming reactor through an amine feeding pipeline. As a result, a slurry containing 1,3-XDA hydrochloride with a concentration of 11.5 wt. % was prepared.

Subsequently, HCl gas was continuously blown into the salt-forming reactor from the HCl feeding pipeline at a feeding rate of 64 parts by mass/hr, and an amine solution containing 1,3-XDA with a concentration of 7.5 wt. % was continuously introduced into the salt-forming reactor from the amine feeding pipeline at a feeding rate of 1000 parts by mass/hr, and at the same time, the slurry containing 1,3-XDA hydrochloride was delivered to a first phosgenation reactor through a hydrochloride delivery pipeline.

Subsequently, phosgene was introduced continuously into first, second, and third phosgenation reactors at the feeding rate shown in Table 1. Table 1 shows the reaction temperature and reaction pressure (gauge pressure) of the three reactors, the feeding proportion of phosgene relative to 1 mol of 1,3-XDA hydrochloride, and the moisture content of reuse solvent.

As a result, 1,3-XDA hydrochloride was reacted with phosgene to produce 1,3-XDI, and a reaction substance containing 1,3-XDI was prepared. In addition, a portion of the unreacted phosgene was condensed into the phosgenation reactor by a condenser.

Subsequently, the phosgenation reaction solution was continuously delivered to a phosgene removal column. Then, the reaction substance was subjected to gas removal process in the phosgene removal column. Then, a gas-removed substance was discharged from the phosgene removal column and continuously delivered to a solvent removal column through a gas-removed substance delivery pipeline. As a result, 120 parts by mass of solvent-removed substance containing 1,3-XDI with a concentration of 95 wt. % were prepared.

Subsequently, the solvent-removed substance was discharged from the solvent removal column through a solvent-removed substance delivery pipeline, and the removed solvent was refined by a solvent refining column and reused.

The solvent refining column was filled with a filler equivalent to a theoretical plate number of 15, which has operating conditions as follows:

bottom temperature: 80-130° C.;

overhead temperature: 60-120° C.;

overhead pressure: as shown in Table 1;

overhead reflux ratio: as shown in Table 1;

residence time: 0.5-10 h; and controlled moisture content in the reuse solvent: as shown in Table 1.

The material with solvent removed was continuously delivered to a tar removal device. Then, the solvent-removed substance was subjected to tar removal in the tar removal device to prepare an intermediate substance. The containing proportions of chlorobenzene (MCB), XDI, IBA and elemental bromine in the intermediate substance are shown in Table 1.

Subsequently, the intermediate substance was continuously delivered to a rectification column at a feeding rate of 100 parts by mass/hr. The rectification column was filled with a filler equivalent to a theoretical plate number of 20. Then, in the rectification column, a light component was removed from the top of the column and an XDI composition product was collected from the middle of the column.

Rectification conditions in the rectification column are as follows:

bottom temperature: 145-160° C.;

overhead temperature: 100-130° C.;

overhead pressure: 0-500 Pa; and residence time: 1-10 h.

Collection amount and overhead reflux ratio of the rectification process are shown in Table 1.

As a result, the XDI composition was prepared. The containing proportions of XDI, IBA and elemental bromine in the XDI composition are shown in Table 1.

Comparative Example 2

The XDJ composition obtained in Example 1 was mixed with the XDJ composition in Comparative Example 3 according to 1:1 under nitrogen protection to obtain the XDJ composition of Comparative Example 2.

Comparative Example 3

The XDJ composition of Comparative Example 3 was prepared according to the Example 1 of U.S. Pat. No. 5,196,572A.

TABLE 1

Conditions and results of Examples 1-7 and Comparative Examples 1-3

| | Parameters | | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|---|---|
| Isocyanation process | phosgene feeding rate | parts/h | 1254 | 1254 | 1472 | 1472 | 1690 | 1690 | 1799 | 2235 | | |
| | phosgene feeding proportion | | 11.5 | 11.5 | 13.5 | 13.5 | 15.5 | 16.5 | 17.5 | 20.5 | | |
| | reaction temperature | ° C. | 145 | 146 | 147 | 148 | 149 | 150 | 151 | 155 | | |
| | reaction pressure | MPaG | 0.15 | 0.15 | 0.16 | 0.16 | 0.20 | 0.20 | 0.20 | 0.20 | | |
| | residence time | h | 7 | 7 | 7 | 7 | 10 | 15 | 20 | 25 | | |
| Solvent refining process | overhead pressure of solvent refining column | Kpa | 70 | 60 | 50 | 70 | 70 | 80 | 90 | 100 | | |
| | reflux ratio of solvent refining column | | 90 | 80 | 70 | 60 | 50 | 40 | 10 | 5 | | |
| | moisture of reuse solvent | ppm | 10 | 40 | 80 | 120 | 240 | 400 | 500 | 600 | | |
| Intermediate substance | chlorobenzene | ppm | 550 | 550 | 550 | 550 | 550 | 550 | 550 | 550 | | |
| | XDI | % | 99.5 | 99.5 | 99.5 | 99.5 | 99.5 | 99.4 | 99.4 | 99.3 | | |
| | IBA | ppm | 0.5 | 7.5 | 14 | 75 | 260 | 410 | 610 | 790 | | |
| | elemental bromine | ppm | 0.8 | 1.5 | 8.6 | 19 | 32 | 54 | 65 | 75 | | |
| Distillation process | collection amount | parts/h | 94 | 93.5 | 93 | 92.5 | 92 | 91.5 | 91 | 90.5 | | |
| | reflux ratio | | 5 | 5.5 | 5 | 6 | 5.5 | 5 | 6 | 5.5 | | |
| XDI Compositions | XDI | % | 99.8 | 99.8 | 99.8 | 99.8 | 99.8 | 99.7 | 99.7 | 99.7 | 99.8 | 99.9 |
| | IBA | ppm | 0.2 | 6 | 12 | 60 | 210 | 320 | 500 | 630 | 0.1 | 0 |
| | elemental bromine | ppm | 0.5 | 0.9 | 6 | 13 | 24 | 36 | 50 | 65 | 0.3 | 0 |

Application Performance Test

The XDI compositions of the examples and comparative examples are prepared into various resin materials and evaluated for performance, which are specifically as follows.

1. Elastomer (TPU)

(1) Preparation Method:

In a four-necked flask equipped with a stirrer, a thermometer, a reflux tube and a nitrogen feeding pipeline, 198 parts by mass of each XDI composition (polyisocyanate component) of Examples 1-7 and Comparative Examples 1, 2 and 3 and 531.2 parts by mass of an adipic acid-based polyester polyol (prepared by Mitsui Chemicals, TAKELAC U-2024, containing a component having an active hydrogen group) with a number-average molecular mass of 2000 were added and reacted at 80° C. under nitrogen atmosphere until an NCO group content became 9.1 wt. %, and an isocyanate-ended prepolymer was prepared.

In addition, 3.9 parts by mass of a heat stabilizer (Ciba Specialty Chemicals, IRGANOX 245) and 0.07 parts by mass of a solution, which was obtained by diluting the catalyst tin octanoate (Innochem Reagent) to 4 wt. % with diisononyl adipate (Xiya Reagent), were added to the isocyanate-ended prepolymer and mixed by stirring at 600 rpm for about 1 minute using a mechanical stirrer (Germany IKA, RW20). Subsequently, 131.9 parts by mass of 1,4-butanediol (Innochem Reagent) as a chain extender, which had been pre-adjusted to 80° C., were added to the isocyanate-ended prepolymer. Further, a mixture of the isocyanate-ended prepolymer and the chain extender was stirred thoroughly for about 2 minutes until the overall mixture became uniform.

Subsequently, the mixture was flowed into a stainless steel tray which had been pre-adjusted to 150° C. and reacted at 150° C. for 1 hour, and then reacted at 100° C. for 23 hours to prepare the elastomer.

Then, the elastomer was taken out from the tray and maintained under a constant temperature and humidity condition at room temperature of 23° C. and 55% relative humidity for 7 days.

(2) Performance evaluation:

The color difference of the obtained elastomer (TPU) is determined by the xenon-lamp irradiation test and the results are shown in Table 2.

2. Optical Material (Plastic Lens Material)

(1) Preparation method:

The 0.001 parts by mass of dibutyltin dichloride, 0.07 parts by mass of internal release agent (prepared by Stepan, ZELECUN, acid phosphate), 0.05 parts by mass of UV absorber (prepared by Sakai Chemical Industry, Biosorb 583), and 36.4 parts by mass of each of the XDI compositions of Examples 1-7 and Comparative Examples 1, 2 and 3 were added to a flask. Then, the system was stirred at 25° C. for 1 hour to dissolve for preparing the polyisocyanate component.

Then, 33.6 parts by mass of 1,2-bis[(2-mercaptoethyl) thio]-3-mercaptopropane (polythiol component) were added to the polyisocyanate component and mixed to prepare the polymeric composition.

The polymeric composition was defoamed at 600 Pa for 1 hour and then filtered through a 3 m PTFE filter. Then, the polymeric composition was injected into a mold formed by a glass mold and tape. The mold was put into an oven and slowly heated from 10° C. to 120° C., and polymerization was performed for 18 hours. After the polymerization, the mold was taken out from the oven, and the optical material was prepared after released form the mold.

(2) Performance evaluation:

The Y.I. of the obtained plastic lens is determined. The results are shown in Table 2.

3. Two-Component Polyurethane Coating Material (Including Agent A and Agent B)

(1) Preparation method:

Preparation of agent A-1:

The 463.3 parts by mass of each of the XDI compositions of Examples 1-7 and Comparative Examples 1, 2 and 3 and 36.7 parts by mass of trimethylolpropane were mixed and reacted at 70° C. for 6 hours under nitrogen atmosphere. The unreacted XDI was distilled off by a film distillation device from the reaction solution to prepare the modified XDI composition. The modified XDI composition contains carbamate groups as a reaction product of XDI and trimethylolpropane.

Ethyl acetate was added to the modified XDI composition in a manner of solid component being 75 wt. % to prepare the polyisocyanate component (agent A-1). It should be noted that an NCO group content of the polyisocyanate component was 11.8 wt. %.

Preparation of agent A-2:

The 100 parts by mass of each of the XDI compositions of Examples 1-7 and Comparative Examples 1, 2 and 3 were added with 2 parts by mass of 1,3-butanediol, and heated to 75° C. under nitrogen atmosphere, and subjected to isocyanation reaction for 2 h. An equivalent ratio of the isocyanate group of XDI to the hydroxyl group of 1,3-butanediol (NCO/OH) was 24.

Subsequently, at the same temperature, as an isocyanuration catalyst, combined with a solution of tetrabutylammonium hydroxide (37% methanol solution) 0.1 phr (converted to 0.037 phr for the solid component), the isocyanuration reaction was stopped after 4 hours. The obtained reaction solution was subjected through a film distillation device (with a temperature of 150° C., a vacuum degree of 50 Pa) to remove the unreacted XDI (with a distillation yield of 60 wt. %), thereby preparing the modified XDI composition. The modified XDI composition contains an isocyanurate group as a trimer of XDI. Ethyl acetate was added to the modified XDI composition in a manner of solid component being 75 wt. % to prepare the polyisocyanate component (agent A-2).

Preparation of agent B:

The 40 parts by mass of fluorine polyol (prepared by DAIKIN INDUSTRIES, LTD., ZEFFLE GK-570, solid composition hydroxyl value: 64 mgKOH/g, solvent: butyl acetate), 52.5 parts by mass of titanium oxide (prepared by Ishihara Sangyo Kaisha, Ltd., CR93), 33.8 parts by mass of butyl acetate and 110 parts by mass of glass beads with a diameter of 2 mm were stirred for 2 hours with a paint stirrer. Then, the glass beads were removed from the mixture by filtration.

After that, a solvent was added in a manner of solid component concentration being 58 wt. % to prepare the component containing an active hydrogen group (agent B). A containing proportion of titanium oxide in the component containing an active hydrogen group is 45 wt. %.

(2) Performance evaluation:

The polyisocyanate component (agent A-1 or agent-2) obtained in a manner of equivalent ratio of the isocyanate group to the hydroxyl group (NCO/OH) being 1.0 and the component containing an active hydrogen group (agent B) were mixed to prepare a mixture. Subsequently, butyl acetate was added to the mixture in a manner of NV value (mass of the coating film composition) being 60%. Then, the mixture was coated on the surface of a polyethylene terephthalate (PET) substrate and cured by heating at 120° C. for 2 minutes. Subsequently, the PET substrate coated with the mixture was maintained at 60° C. for 2 days. As a result, a coating layer with a thickness of about 15 m was formed on the PET substrate.

The weather resistance of the coating layer (color difference Δb (=|b2−b1|) of the coating layer in the damp and hot resistance test) was determined. The results are shown in Table 2.

TABLE 2

Application effect data of XDI composition

| Parameters | | | Example 1 | Example 2 | Example 3 | Example 4 | Example 5 | Example 6 | Example 7 | Comparative Example 1 | Comparative Example 2 | Comparative Example 3 |
|---|---|---|---|---|---|---|---|---|---|---|---|---|
| XDI Composition | XDI | % | 99.8 | 99.8 | 99.8 | 99.8 | 99.8 | 99.7 | 99.7 | 99.7 | 99.8 | 99.9 |
| | IBA | ppm | 0.2 | 6 | 12 | 60 | 210 | 320 | 500 | 630 | 0.1 | 0 |
| | elemental bromine | ppm | 0.5 | 0.9 | 6 | 13 | 24 | 36 | 50 | 65 | 0.3 | 0 |
| TPU | xenon irradiation test | b1 | 0.51 | 0.52 | 0.55 | 0.56 | 0.53 | 0.55 | 0.54 | 0.6 | 0.54 | 0.5 |
| | | b2 | 3.1 | 3.2 | 3.2 | 3.3 | 3.5 | 3.4 | 3.5 | 5 | 4.5 | 4.6 |
| | | Δb | 2.59 | 2.68 | 2.65 | 2.74 | 2.97 | 2.85 | 2.96 | 4.4 | 3.96 | 4.1 |
| Lens | yellowness index YI | YI | 1.6 | 1.61 | 1.62 | 1.62 | 1.64 | 1.65 | 1.67 | 1.8 | 1.72 | Gel |
| Coating agent | agent A-1 | b1 | 0.34 | 0.33 | 0.4 | 0.35 | 0.35 | 0.35 | 0.35 | 0.45 | 0.35 | 0.35 |
| | | b2 | 2.16 | 2.09 | 2.18 | 2.08 | 2.16 | 2.18 | 2.26 | 3.56 | 2.87 | 2.98 |
| | | Δb | 1.82 | 1.76 | 1.78 | 1.73 | 1.81 | 1.83 | 1.91 | 3.11 | 2.52 | 2.63 |
| | agent A-2 | b1 | 0.36 | 0.35 | 0.42 | 0.38 | 0.37 | 0.41 | 0.39 | 0.48 | 0.35 | 0.35 |
| | | b2 | 2.2 | 2.16 | 2.12 | 2.12 | 2.19 | 2.27 | 2.3 | 3.28 | 2.36 | 2.46 |
| | | Δb | 1.84 | 1.81 | 1.7 | 1.74 | 1.82 | 1.86 | 1.91 | 2.8 | 2.01 | 2.11 |

As can be seen from Table 1, the present application can effectively improve the color-changing resistance of the resin prepared from the composition by controlling the IBA content of the XDI composition within 0.2-500 ppm; when the IBA content is higher than 500 nm (Comparative Example 1) or lower than 0.2 ppm (Comparative Example 2), or no IBA is contained at all, the color-changing resistance is worse than the present application. The XDI composition provided in the present application has outstanding application prospects among various resin materials.

What is claimed is:

1. A xylylene diisocyanate composition, comprising xylylene diisocyanate and 0.2-500 ppm of a compound as shown in formula (1):

(1)

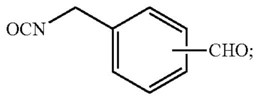

wherein the xylylene diisocyanate composition further comprises a bromine-containing compound; and the content of the bromine-containing compound is 0.5-50 ppm based on a mass of elemental bromine.

2. The xylylene diisocyanate composition according to claim 1, wherein the xylylene diisocyanate comprises any one or a combination of at least two of 1,2-bis (isocyanatomethyl) benzene, 1,3-bis (isocyanatomethyl) benzene or 1,4-bis (isocyanatomethyl) benzene.

3. The xylylene diisocyanate composition according to claim 2, wherein the xylylene diisocyanate comprises 1,3-bis (isocyanatomethyl) benzene and/or 1,4-bis (isocyanatomethyl) benzene.

4. The xylylene diisocyanate composition according to claim 2, wherein the xylylene diisocyanate is 1,3-bis (isocyanatomethyl) benzene.

5. The xylylene diisocyanate composition according to claim 1, wherein the compound as shown in formula (1) comprises any one or a combination of at least two of the following compounds:

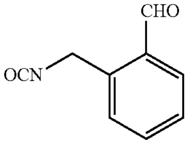,

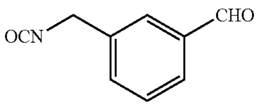

or

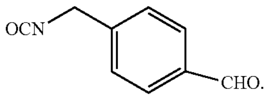

6. A preparation method for the xylylene diisocyanate composition according to claim 1, comprising:

(1) isocyanation process: subjecting xylylenediamine or xylylenediamine hydrochloride to isocyanation reaction with phosgene in the presence of a reaction solvent to obtain a reaction product containing xylylene diisocyanate and the compound as shown in formula (1);

(2) solvent separation and refining process: removing the solvent from the reaction product obtained in step (1), and refining the removed solvent to obtain a reuse solvent and then returning to the reaction system in step (1); and (3) separation process: separating and purifying a solvent-removed reaction product obtained in step (2) to obtain the xylylene diisocyanate composition.

7. The preparation method according to claim 6, wherein the reaction solvent comprises a fresh solvent and/or a reuse solvent.

8. The preparation method according to claim 6, wherein the moisture content of the reaction solvent is 1-500 ppm.

9. The preparation method according to claim 6, wherein the moisture content of the reuse solvent is 1-500 ppm.

10. A modified composition of a xylylene diisocyanate composition, which is obtained by modifying the xylylene diisocyanate composition according to claim 1, wherein a modified xylylene diisocyanate of the modified composition comprises any one or a combination of at least two of groups (a)-(i) as follows: (a) an isocyanurate group, (b) a uretdione group, (c) a biuret group, (d) a carbamate group, (e) a ureido group, (f) an iminooxadiazinedione group, (g) an allophanate group, (h) a uretonimine group or (i) a carbodiimide group.

11. A two-component polyurethane raw material comprising agent A and agent B;

the agent A comprises the xylylene diisocyanate composition according to claim 1 and/or a modified composition; wherein the modified composition is obtained by modifying the xylylene diisocyanate composition according to claim 1, wherein a modified xylylene diisocyanate of the modified composition comprises any one or a combination of at least two of groups (a)-(i) as follows: (a) an isocyanurate group, (b) a uretdione group, (c) a biuret group, (d) a carbamate group, (e) a ureido group, (f) an iminooxadiazinedione group, (g) an allophanate group, (h) a uretonimine group or (i) a carbodiimide group;

the agent B comprises a substance having an active hydrogen group.

12. A polyurethane resin which is obtained by reacting the xylylene diisocyanate composition according to claim 1 with a substance having an active hydrogen group, or by reacting a modified composition with a substance having an active hydrogen group;

wherein the modified composition is obtained by modifying the xylylene diisocyanate composition according to claim 1, wherein a modified xylylene diisocyanate of the modified composition comprises any one or a combination of at least two of groups (a)-(i) as follows: (a) an isocyanurate group, (b) a uretdione group, (c) a biuret group, (d) a carbamate group, (e) a ureido group, (f) an iminooxadiazinedione group, (g) an allophanate group, (h) a uretonimine group or (i) a carbodiimide group.

13. An elastomer material comprising the polyurethane resin according to claim 12.

14. An optical material which is obtained by polymerizing the xylylene diisocyanate composition according to claim 1 with a polythiol compound, or by polymerizing a modified composition with a polythiol compound;

wherein the modified composition is obtained by modifying the xylylene diisocyanate composition according to claim 1, wherein a modified xylylene diisocyanate of the modified composition comprises any one or a combination of at least two of groups (a)-(i) as follows: (a) an isocyanurate group, (b) a uretdione group, (c) a biuret group, (d) a carbamate group, (e) a ureido group, (f) an iminooxadiazinedione group, (g) an allophanate group, (h) a uretonimine group or (i) a carbodiimide group.

15. The optical material according to claim 14, wherein the optical material comprises a plastic lens material, a vehicle lampshade material, a transparent roof material, or a lens material for smartphones or tablets.

* * * * *